US009150926B2

(12) United States Patent
Kebebew et al.

(10) Patent No.: US 9,150,926 B2
(45) Date of Patent: Oct. 6, 2015

(54) DIAGNOSIS AND TREATMENT OF ADRENOCORTICAL TUMORS USING HUMAN MICRORNA-483

(75) Inventors: Electron Kebebew, Rockville, MD (US); Erin Patterson, Kensington, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 713 days.

(21) Appl. No.: 12/961,298

(22) Filed: Dec. 6, 2010

(65) Prior Publication Data

US 2012/0142753 A1    Jun. 7, 2012

(51) Int. Cl.
| | |
|---|---|
| *C12Q 1/68* | (2006.01) |
| *C12P 19/34* | (2006.01) |
| *C12N 5/00* | (2006.01) |
| *C12N 5/02* | (2006.01) |
| *C12N 15/113* | (2010.01) |

(52) U.S. Cl.
CPC .......... *C12Q 1/6886* (2013.01); *C12N 15/113* (2013.01); *C12N 2310/113* (2013.01); *C12N 2310/141* (2013.01); *C12Q 2600/106* (2013.01); *C12Q 2600/112* (2013.01); *C12Q 2600/118* (2013.01); *C12Q 2600/136* (2013.01); *C12Q 2600/178* (2013.01)

(58) Field of Classification Search
USPC .......................................... 514/44; 536/24.5
See application file for complete search history.

(56) References Cited

FOREIGN PATENT DOCUMENTS

WO    WO 2010/070637    6/2010

OTHER PUBLICATIONS

Doghman et al. (Cancer Research, 2010, vol. 70:4666-4675).*
Almeida et al. (Journal of Clinical Endocrinology Metabolism, 2008 vol. 93:3524-3531).*
Tömböl et al. (Endocrine-Related Cancer (2009) 16:895-906).*
Soon et al. (Endocrine-Related Cancer (2009) 16:573-83).*
Iliopoulos et al. (Cancer Research, 2009 69(8):3278-3282).*
Patterson et al., "MicroRNA Profiling of Adrenocortical Tumors Reveals miR-483 as a Marker of Malignancy," *Cancer*, 10 pages, 2010.
Patterson et al., "Genome-Wide MicroRNA Profiling of Adrenocortical Tumors Identifies miR-483-5p as a Marker of Malignancy," Poster Presentation on Jun. 17, 2010 at Adrenal 2010, 1 page.
Soon et al., "miR-195 and miR-483-5p Identified as Predictors of Poor Prognosis in Adrenocortical Cancer," *Clinical Cancer Research*, 15:24, Abstract only, 2 pages, 2009.

\* cited by examiner

*Primary Examiner* — Terra C Gibbs
(74) *Attorney, Agent, or Firm* — Klarquist Sparkman, LLP

(57) ABSTRACT

Disclosed herein are methods of diagnosing and treating a malignant adrenocortical tumor, including adrenocortical carcinoma. In some examples, methods of diagnosing a malignant adrenocortical tumor include detecting expression of at least one microRNA (miR) gene product, such as miR-100, miR-125b, miR-195, miR-483-3p, miR-483-5p and IGF2 mRNA in a sample obtained from the subject with an adrenocortical tumor and comparing expression of at least one of these miR gene products and IGF2 mRNA in the sample obtained from the subject to a control. Altered expression of at least one of the miR gene products and IGF2 mRNA, such as a decrease in miR-100, miR-125b or miR-195 or an increase in miR-483-3p, miR-483-5p, and an increase in IGF2 mRNA, in the sample obtained from the subject compared to the control indicates a malignant adrenocortical tumor.

10 Claims, 6 Drawing Sheets

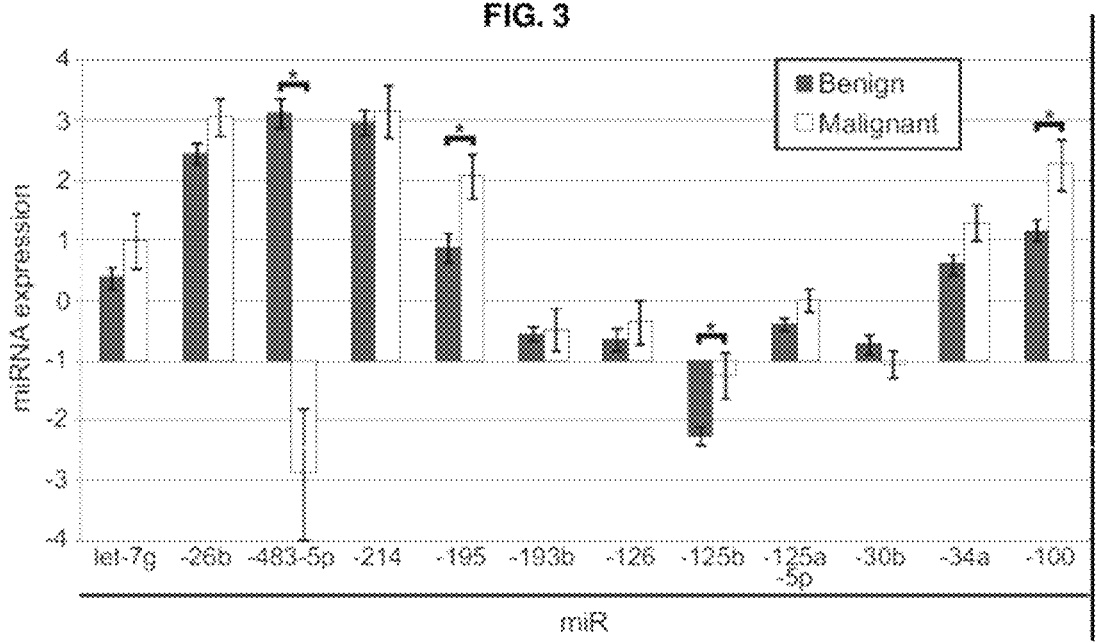

DIAGNOSIS AND TREATMENT OF ADRENOCORTICAL TUMORS USING HUMAN MICRORNA-483

FIELD OF THE DISCLOSURE

This disclosure concerns microRNAs (miRNAs or miRs) and mRNAs that are differentially expressed in adrenocortical tumors, and use of the disclosed miRNAs, such as miR-483-5p, and mRNAs, such as IGF2 mRNA, for the diagnosis and treatment of malignant adrenocortical tumors.

BACKGROUND

Adrenocortical carcinoma (ACC) is a rare but aggressive malignancy of the adrenal cortex. This cancer affects 1 to 2 people per million per year and accounts for 0.02-0.2% of all cancer deaths. Approximately half of all patients have metastatic disease at the time of diagnosis resulting in an average five-year survival of less than 10%. Currently, there is limited knowledge regarding the initiation and pathophysiology of ACC and a lack of effective therapies to treat this disease.

Benign adrenocortical tumors are a much more common occurrence with approximately 5% of people over 50 years old having at least one adrenal mass. These tumors often share many imaging characteristics with their ACC counterparts and therefore determining if a tumor is benign or malignant is not always straightforward. Metastatic disease or local invasion is the only absolute indicator of malignancy. Masses without these features are assessed preoperatively based on size, and imaging characteristics, although the findings of these studies often are unable to definitively categorize the tumor as benign or malignant. After resection, tumor pathology is assessed based on several histologic criteria including cell morphology, cellular proliferation, and tumor invasiveness (Weiss criteria). However for some tumors, with some suspicious features, a definitive diagnosis may not be possible. Accurate diagnosis is critical since the prognosis, follow up, and therapeutic strategy for ACC is much different than that for a benign tumor. Therefore, there is a need for better diagnostic tools for assessing adrenocortical tumors, preoperatively and as an adjunct to routine histopathology.

SUMMARY OF THE DISCLOSURE

MicroRNAs are small, single-stranded RNA molecules that post-transcriptionally regulate gene expression by directly targeting mRNAs and affecting their stability and/or translation. These regulators are involved in a wide range of normal physiologic and pathologic processes. MicoRNA expression profiling has been performed on many types of human cancers and indicates that malignancy involves miRNA dysregulation and that particular miRNA expression signatures could be useful for molecular diagnosis and/or prognosis. Additionally, functional studies suggest that aberrant miRNA expression contributes to cancer pathogenesis making these molecules potential targets for cancer therapy.

It is disclosed herein that malignant adrenocortical tumors exhibit differential miR gene expression as compared to benign adrenocortical tumors. In particular, it is disclosed that miR-100, miR-125b, and miR-195 are decreased and miR-483-3p and miR-483-5p expression are increased in ACC. Moreover, it is reported herein that the expression level of miR-483-5p alone can accurately diagnose an adrenocortical tumor as benign or malignant. Additionally, IGF2 mRNA expression is disclosed to be increased in malignant adrenocortical tumors.

Thus, provided herein are methods of diagnosing a malignant adrenocortical tumor, including ACC. In one embodiment, the method includes detecting expression of at least one miR gene product listed in Table 2 or FIG. 2 and IGF2 mRNA in a sample obtained from the subject with an adrenocortical tumor; comparing expression of at least one of the miR gene products listed in Table 2 or FIG. 2 and IGF2 mRNA in the sample obtained from the subject to a control, wherein altered expression of at least one of the miR gene products listed in Table 2 or FIG. 2 and IGF2 mRNA in the sample obtained from the subject compared to the control indicates a malignant adrenocortical tumor. In some examples, the at least one miR gene product includes miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5, miR-786-3p or any combination thereof. In other examples, the at least one miR gene product includes miR-483-5p. In further examples, the at least one miR gene product includes miR-100, miR-125b, miR-195, miR-483-3p, miR-483-5p or a combination thereof. In some examples, altered expression of at least one of the miR gene products listed in Table 2 or FIG. 2 includes increased expression, such as an at least 2-fold increase in expression in at least one of miR-665, miR-1246, miR-483-5p, miR-483-3p, miR-642, miR-1308 or a combination thereof and IGF2 mRNA. In some examples, altered expression of at least one of the miR gene products listed in Table 2 includes decreased expression, such as an at least 2-fold decrease in at least one of miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p or a combination thereof as compared to the control (such as a benign adrenocortical tumor).

Also provided are methods of treating a malignant adrenocortical tumor in a subject. In some examples, a method of treatment includes administering to the subject a therapeutically effective amount an agent that alters the expression of at least one miR gene product listed in Table 2, FIG. 2 and/or IGF2 mRNA, thereby treating the malignant adrenocortical tumor. In some examples, the agent inhibits expression of a miRNA gene product and/or IGF2 mRNA that are up-regulated in a malignant adrenocortical tumor. For example, the agent is an antisense compound (such as an antisense oligonucleotide, siRNA or ribozyme) specific for at least one of the miR gene products that is up-regulated in the malignant adrenocortical tumor (such as miR-483-3p, miR-483-5p or a combination thereof) and/or IGF2 mRNA. In some examples, the method is used for treating a subject with ACC.

Further provided are methods of determining the effectiveness of an agent for the treatment of a malignant adrenocortical tumor in a subject with the malignant adrenocortical tumor. In some examples, this method includes detecting expression of at least one miR gene product listed in Table 2 and/or FIG. 2 and IGF2 mRNA in a sample from the subject following treatment with the agent; and comparing expression of the at least one miR gene product listed in Table 2 and/or FIG. 2 and IGF2 mRNA following treatment to a reference value, wherein an alteration in the expression of the at least one miR gene product listed in Table 2 and/or FIG. 2 and IGF2 mRNA following treatment indicates that the agent is effective for the treatment of the malignant adrenocortical tumor in the subject. In some examples, the reference value represents an expression value of the at least one miR gene product listed in Table 2 and/or FIG. 2 and IGF2 mRNA in a sample from the subject prior to treatment with the agent. In some examples, the at least one miR gene product is miR-483-5p or miR-483-3p and an at least two-fold decrease in the expression of miR-483-5p or miR-483-3p and IGF2 mRNA following treatment indicates that the agent is effective for the treatment of the malignant adrenocortical tumor in the subject.

The foregoing and other features of the disclosure will become more apparent from the following detailed description of a several embodiments which proceeds with reference to the accompanying figures.

BRIEF DESCRIPTION OF THE FIGURES

FIG. 2 is a graph showing miRNAs significantly up- or down-regulated in ACC as compared to benign adrenocortical tumors. miRNAs significantly up- or down-regulated in ACC as compared to benign adrenocortical tumors were identified as those that were statistically significantly different (p<0.01, Ho: there is no difference between the expression in benign and malignant tumors) and had an expression difference of at least two-fold (up or down) between the two tumor classes were classified as the most differentially expressed. 23 miRNAs fit this criteria and the fold change for each is plotted (negative values indicate decreased expression in malignant and positive values indicate increased expression in malignant). The underlined miRNAs were chosen to be validated by real-time quantitative RT-PCR.

FIG. 3 is a graph showing real-time quantitative RT-PCR was used to assay the expression of various miRNAs in tumor samples. The expression of each miRNA is expressed as the $\Delta C_t$ ($C_t$ miR of interest–$C_t$ RNU48). The mean expression was calculated for benign tumors (n=24, except miRs-483-5p, 193b, and -125-5p where n=23) and ACCs (n=10) and is plotted (±standard error of the mean). An increase in $\Delta C_t$ indicated lower expression whereas a decrease in AC, indicated higher expression (comparing benign to malignant). A statistically significant difference between benign and malignant was indicated with an asterisk (*) (p<0.05, Mann Whitney U test).

FIG. 6A shows MiR-483-3p expression, expressed as the $\Delta C_t$ ($C_t$ miR-483-3p–$C_t$ RNU48), is plotted against the $\Delta C_t$ of miR-483-5p for each patient sample. A strong positive correlation was detected (r=0.965, Pearson correlation). FIG. 6B shows IGF2 expression, as the $\Delta C_t$ ($C_t$ IGF2–$C_t$ GAPDH), is plotted against the $\Delta C_t$ of miR-483-5p ($C_t$ miR-483-5p–$C_t$ RNU48) for each patient sample. Real-time quantitative RT-PCR was used to assay the expression of IGF2 mRNA in tumor samples, either benign (n=19) or malignant (primary, n=2; ACC metastasis, n=27; ACC recurrence, n=3). A significant positive correlation was detected (r=0.799, Pearson correlation).

DETAILED DESCRIPTION OF SEVERAL EMBODIMENTS

I. Terms

Figure 1:
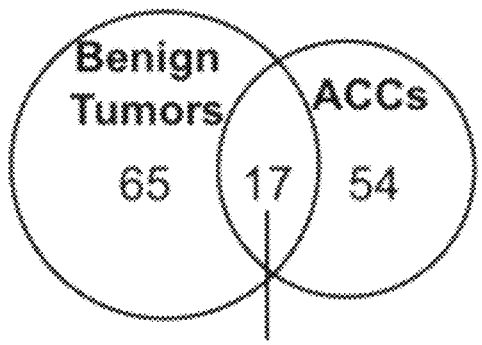
FIG. 1 is a schematic illustrating miRNAs significantly up- or down-regulated in malignant and/or benign adrenocortical tumors as compared to normal adrenocortical tissue. Microarray analysis compared tumors (benign or malignant) to normal adrenocortical tissue. Differentially expressed genes were defined as those that had a p-value <0.01 (Ho: there is no difference between expression in tumor and normal). 17 miRNAs were misexpressed in both benign and malignant tumors (listed in the box, bold and italics indicate lower and higher expression in tumors, respectively). The underlined miRNAs were chosen to be validated by real-time quantitative RT-PCR.

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment. For example, adjunctive therapy includes chemotherapy or radiation that is administered following surgical resection of cancerous tissue.

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Adrenocortical carcinoma (ACC): A rare but aggressive malignancy of the adrenal cortex. Adrenocortical carcinoma (also called "adrenal carcinoma) is cancer that affects 1 to 2 people per million per year and accounts for 0.02-0.2% of all cancer deaths. Approximately half of all patients have metastatic disease at the time of diagnosis resulting in an average five-year survival of less than 10%. Currently there is limited knowledge regarding the initiation and pathophysiology of ACC.

Metastatic disease or local invasion is the only absolute indicator of malignancy. Masses without these features are assessed preoperatively based on size, and imaging characteristics, although the findings of these studies often are unable to definitively categorize the tumor as benign or malignant. After resection, tumor pathology is assessed based on several histologic criteria including cell morphology, cellular proliferation, and tumor invasiveness (Weiss criteria). The only curative treatment is complete surgical excision of the tumor, which can be performed even in the case of invasion into large blood vessels, such as the renal vein or inferior vena cava. A large percentage of patients are not surgical candidates. Radiation therapy and radiofrequency ablation may be used for palliation in patients who are not surgical candidates.

Chemotherapy regimens typically include the drug mitotane, an inhibitor of steroid synthesis which is toxic to cells of the adrenal cortex, as well as standard cytotoxic drugs. One widely used regimen consists of cisplatin, doxorubicin, etoposide, and mitotane. The endocrine cell toxin streptozotocin has also been included in some treatment protocols. Chemotherapy may be given to patients with unresectable disease, to shrink the tumor prior to surgery (neoadjuvant chemotherapy), or in an attempt to eliminate microscopic residual disease after surgery (adjuvant chemotherapy). Hormonal therapy with steroid synthesis inhibitors such as aminoglutethimide may be used in a palliative manner to reduce the symptoms of hormonal syndromes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including inhibiting or treating a malignant adrenocortical tumor, such as inhibiting or treating ACC).

Alteration in expression: An alteration in expression of a miR gene product refers to a change in the level of the miR gene product that is detectable in a biological sample (such as a sample from a malignant adrenocortical tumor) relative to a control (such as a benign adrenocortical tumor or normal (non-cancerous and non-tumor) adrenocortical tissue). An "alteration" in expression includes an increase in expression (up-regulation) or a decrease in expression (down-regulation).

Antisense compound: Refers to an oligomeric compound that is at least partially complementary to the region of a target nucleic acid molecule (such as a miR gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is a miR gene product (such as those indicated as upregulated in Table 2).

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such nucleic acid molecules), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least 2, at least 5, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-1000 addressable locations, such as 10-100 addressable locations. In particular examples, an array consists essentially of probes or primers (such as those that permit amplification) specific for the miR gene products listed in one or more of Table 2, FIG. 2 and FIG. 3.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biological sample: A biological specimen containing genomic DNA, RNA (including mRNA and microRNA), protein, or combinations thereof, obtained from a subject. Examples include, but are not limited to, saliva, peripheral blood, urine, tissue biopsy, surgical specimen, and autopsy material. In one example, a sample includes a biopsy of an adrenal cortex, such as from a patient with a malignant or benign adrenocortical tumor or a healthy control subject. In other embodiments, the biological sample is blood, or a component thereof, such as plasma or serum.

Blood: The fluid that circulates through the heart, arteries, capillaries, and veins and is the chief means of transport (such as for transport of gases, metabolites and waste products) within the body. Blood is primarily composed of plasma (the fluid portion) and blood cells and platelets (the solid portion). "Plasma" refers to the fluid portion of the blood, in which the blood cells are suspended. Plasma is mostly water and contains plasma proteins, inorganic salts, nutrients, gases, waste materials from the cells, and various hormones, secretions and enzymes. "Serum" refers to the clear, straw-colored, liquid portion of the plasma that does not contain fibrinogen or blood cells, and remains fluid after clotting of blood.

Chemotherapeutic agents: Any chemical agent with therapeutic usefulness in the treatment of diseases characterized by abnormal cell growth. Such diseases include tumors, neoplasms, and cancer, including ACC. In some cases, a chemotherapeutic agent is a radioactive compound. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): Oncology Pocket Guide to Chemotherapy, 2nd ed. St. Louis, Mosby-Year Book, 1995; Fischer, D. S., Knobf, M. F., Durivage, H. J. (eds): The Cancer Chemotherapy Handbook, 4th ed. St. Louis, Mosby-Year Book, 1993). Combination chemotherapy is the administration of more than one agent to treat cancer.

Contacting: Placement in direct physical association, including both a solid and liquid form. Contacting an agent with a cell can occur in vitro by adding the agent to isolated cells or in vivo by administering the agent to a subject.

Control: A "control" refers to a sample or standard used for comparison with a test sample, such as a tissue sample obtained from a patient with a benign adrenocortical tumor. In some embodiments, the control is a sample obtained from a healthy patient (also referred to herein as a "normal" control), such as a normal adrenocortical sample. In some embodiments, the control is a historical control or standard value (i.e. a previously tested control sample or group of samples that represent baseline or normal values, such as baseline or normal values in a benign adrenocortical tumor).

Decrease: To reduce the quality, amount, or strength of something. In one example, a therapy decreases a tumor (such as the size of a tumor, the number of tumors, the metastasis of a tumor, or combinations thereof), or one or more symptoms associated with a tumor, for example as compared to the response in the absence of the therapy (such as a therapy administered to affect tumor size via administration of an agent capable of decreasing miRNA-483-5p, miRNA-483-5p or IGF2 mRNA and/or increasing miRNA-100, miRNA-125b or miRNA-195). In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, and biopsy.

Diagnostically significant amount: As used herein a "diagnostically significant amount" refers to an increase or decrease in the level of a miR gene product in a biological sample that is sufficient to allow one to distinguish one patient population from another (such as a malignant adrenocortical tumor from a benign adrenocortical tumor). In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control. In some examples, the diagnostically significant amount is the fold-change in miR or mRNA expression levels shown in the Example Section, such as at least a 2-fold change in miR-100, miR-125b, miR-195, miR-483-3p and/or miR-483-5p (such as an at least 2-fold decrease in miR-100, miR-125b, or miR-195 and an at least 2-fold increase in miR-483-3p and/or miR-483-5p expression) or at least a 2-fold change in IGF2 mRNA expression (such as an at least 2-fold increase in IGF2 mRNA) relative to a RNU48 control. A diagnostically significant amount can also be determined by calculating the fold-change in expression of a particular miR between two sample types (such as between a benign and malignant adrenocortical tumor). Microarray analysis is provided herein as one example of how miR gene product expression can be detected. However, one of skill in the art will recognize that other methods exist to measure gene expression (such as one of the methods described herein) and variation in detected expression levels can occur depending on the method that is used. Thus, the diagnostically significant amount may vary if another method of detection is used, such as RT-PCR.

Differential expression or altered expression of a microRNA: A difference, such as an increase or decrease, in the conversion of the information encoded in a microRNA gene into microRNA gene product. In some examples, the difference is relative to a control or reference value, such as an amount of microRNA expression in a sample from a healthy control subject or a benign adrenocortical tumor.

Downregulated or decreased: When used in reference to the expression of nucleic acid molecules (such as a microRNA or mRNA), refers to any process which results in a decrease in production of a gene product. In the context of the present disclosure, a gene product can be a primary transcript microRNA (pri-miRNA), precursor microRNA (pre-miRNA), mature microRNA or mRNA. Gene downregulation includes any detectable decrease in the production of a microRNA or mRNA. In certain examples, production of a microRNA or mRNA decreases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to diagnosis and/or prognosis a subject with a malignant adrenocortical tumor.

The expression of a nucleic acid molecule can be altered relative to a normal (wild type) nucleic acid molecule. Alterations in gene expression, such as differential expression, include but are not limited to: (1) overexpression; (2) under-expression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have cancer, such as ACC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Gene expression profile (or fingerprint or signature): Differential or altered gene expression can be detected by changes in the detectable amount of gene expression (such mRNA or microRNA) or by changes in the detectable amount of proteins expressed by those genes. A gene expression profile is a distinct or identifiable pattern of gene expression, for instance a pattern of high and low expression of a defined set of genes. In some examples, as few as one or two genes or gene products provides a profile, but more genes or gene products can be used in a profile, for example at least 5, at least 10, at least 15, at least 20, at least 25, at least 30, at least 40 or at least 50. A gene expression profile (also referred to as a fingerprint or signature) can be linked to a tissue or cell type (such as a adrenocortex tissue sample), to a particular stage of a disease, or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have an adrenocortical tumor or a malignant adrenocortical tumor (e.g., the subject has a benign adrenocortical tumor). In some examples, a gene expression profile in a subject is read on an array (such as a nucleic acid array).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each.

IGF2: The protein encoded by this gene acts as a growth promoting hormone that is found under physiological conditions (such as during gestation) and pathophysiological conditions (such as produced in excess by tumors). In particular examples, expression of IGF2 is altered in an adrenocortical tumor, such as increased. The term IGF2 includes any IGF2 gene, cDNA, mRNA, or protein from any organism and that is IGF2 and is expressed in an adrenocortical tumor.

Nucleic acid and protein sequences for IGF2 are publicly available. For example, GENBANK® Accession Nos. NM_000612 (human) and NM_010514 (mouse) disclose IGF2 nucleic acid sequences, and GENBANK® Accession Nos. NP_000603 (human) and NP_034644 (mouse) disclose IGF2 protein sequences, all of which are incorporated by reference as provided by GENBANK® on Dec. 6, 2010.

In one example, IGF2 includes a full-length wild-type (or native) sequence, as well as IGF2 allelic variants that retain the ability to be expressed at increased levels in an adrenocortical tumor and/or modulate an activity of an adrenocortical tumor, such as tumor growth. In certain examples, IGF2 has at least 80% sequence identity, for example at least 85%, 90%, 95%, or 98% sequence identity to IGF2 shown in the Genbank accession numbers above and retain the ability to be expressed at increased levels in an adrenocortical tumor and/or modulate an activity of an adrenocortical tumor, such as tumor growth.

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Malignant: Cells that have the properties of anaplasia invasion and metastasis.

Measuring the level of expression: As used herein, measuring the level of expression of a particular miR or mRNA refers to quantifying the amount of the miR or mRNA present in a sample. Quantification can be either numerical or relative. Detecting expression of the miR or mRNA can be achieved using any method known in the art or described herein, such as by RT-PCR. Detecting expression of a miR or mRNA includes detecting expression of either a mature form of the miR or a precursor form (i.e., a pri-miRNA or pre-miRNA) that is correlated with expression of the miR. Typically, miR detection methods involve sequence specific detection, such as by RT-PCR. miR-specific primers and probes can be designed using the precursor and mature miR nucleic acid sequences that are known in the art (the miRBase microRNA database is available online by the University of Manchester at www.mirbase.org).

In primary embodiments, the change detected is an increase or decrease in expression as compared to a control, such as a reference value or a healthy control subject. In some examples, the detected increase or decrease is an increase or decrease of at least two-fold compared with the control. In other examples, the detected increase or decrease is a change rounded down to the nearest whole number (so that both 2.05 and 2.67 are rounded down to 2) of the fold change shown for a miR in the Example Section, or is rounded to the nearest whole number (so that 2.05 would be rounded to 2 and 2.67 would be rounded to 3). In other embodiments of the methods, the increase or decrease is of a diagnostically significant amount, which refers to a change of a sufficient magnitude to provide a statistical probability of the diagnosis.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). The term "microRNA gene product" includes pri-miRNAs, pre-miRNAs and mature microRNAs (including minor mature miRNA species referred to as miR*).

MicroRNAs modulate gene expression by promoting cleavage of target mRNAs or by blocking translation of the cellular transcript. Thus far, over 900 unique human microRNAs (referred to as hsa-miR) have been identified. Numerous human viral miRs have also been identified, including miRs from Epstein-Barr virus (ebv-miR), Kaposi's sarcoma herpes virus (kshv-miR), herpes simplex virus-1 (hsv1-miR), human immunodeficiency virus-1 (hiv1-miR) and human cytomegalovirus (hcmv-miR). Viral miRs have been identified in human cells and, in some cases, have been linked to human disease, such as cancer.

As new microRNAs are identified, researchers register the sequences prior to publication of their work to ensure that each unique microRNA is assigned an official number (the miRBase Registry is available online through the University of Manchester at www.mirbase.org), eliminating any ambiguity in the literature regarding the identity of particular microRNAs. All miRs referred to by their miRBase registry numbers are herein incorporated by reference as they appear in the miRBase registry as of the filing date of this application. The miRBase registry also provides sequence information for known miRs.

MicroRNA-100: A small non-coding RNA located on human chromosome 11. MicroRNA-100 is also known as miR-100, miRNA100 and hsa-mir-100. The expression of miR-100 is disclosed herein to be linked to malignant adrenocortical tumors. Mir-100 expression is decreased in malignant adrenocortical tumors as compared to benign adrenocortical tumors.

miR-100 sequences are publicly available, for example, GENBANK® Accession numbers NR_031858.1 (rat), NR_029790.1 (mouse), or NR_029515.1 (human) and miRBase Accession numbers MI0000102, MIMAT0000098, MIMAT0004512 or MI0000102, each of which is incorporated by reference in its entirety as available on GENBANK® or miRBase, respectively, on Dec. 6, 2010. One skilled in the art will appreciate that miR-100 nucleic acid molecules can vary from those publicly available, such as polymorphism resulting in one or more substitutions, deletions, insertions, or combinations thereof, while still retaining miR-100 biological activity (e.g., decreased levels of expression being associated with a malignant adrenocortical tumor).

MicroRNA-125b: A small non-coding RNA located on human chromosome 11. MicroRNA-125b is also known as miR-125b, miRNA125b and hsa-mir-125b. The expression of miR-125b is disclosed herein to be linked to malignant adrenocortical tumors. Mir-125b expression is decreased in malignant adrenocortical tumors as compared to benign adrenocortical tumors.

miR-125b sequences are publicly available, for example, GENBANK® Accession number NR_029671 (human) or miRBase Accession number MI0000446, each of which is incorporated by reference in its entirety as available on GENBANK® or miRBase, respectively, on Dec. 6, 2010. One skilled in the art will appreciate that miR-125b nucleic acid molecules can vary from those publicly available, such as a polymorphism resulting in one or more substitutions, deletions, insertions, or combinations thereof, while still retaining miR-125b biological activity (e.g., decreased levels of expression being associated with a malignant adrenocortical tumor).

MicroRNA-195: A small non-coding RNA located on human chromosome 17. MicroRNA-195 is also known as miR-195, miRNA195 and hsa-mir-195. The expression of miR-195 is disclosed herein to be linked to malignant adrenocortical tumors. Mir-195 expression is decreased in malignant adrenocortical tumors as compared to benign adrenocortical tumors.

miR-195 sequences are publicly available, for example, GENBANK® Accession numbers NR_031912.1 (rat), NR_029581 (mouse), or NR_029712.1 (human) and miRBase Accession numbers MI0000489 or MIMAT0004615, each of which is incorporated by reference in its entirety as available on GENBANK® or miRBase, respectively, on Dec. 6, 2010. One skilled in the art will appreciate that miR-195 nucleic acid molecules can vary from those publicly available, such as polymorphisms resulting in one or more substitutions, deletions, insertions, or combinations thereof, while still retaining miR-195 biological activity (e.g., decreased levels of expression being associated with a malignant adrenocortical tumor).

MicroRNA-483-3p: A small non-coding RNA located on human chromosome 11. MicroRNA-483-3p is also known as miR-483-3p, miRNA483-3p and hsa-mir-483-3p. The expression of miR-483-3p is disclosed herein to be linked to malignant adrenocortical tumors. Mir-483-3p expression is increased in malignant adrenocortical tumors as compared to benign adrenocortical tumors.

miR-483-3p sequences are publicly available, for example, GENBANK® Accession number NR_030158 (human miR-483-3p, nucleic acids 48-68) or NR_030251 (mouse miR- 483-3p) and miRBase Accession numbers MIMAT0003173 or MI0002467, each of which is incorporated by reference in its entirety as available on GENBANK® or miRBase, respectively, on Dec. 6, 2010. One skilled in the art will appreciate that miR-483-3p nucleic acid molecules can vary from those publicly available, such as polymorphisms resulting in one or more substitutions, deletions, insertions, or combinations thereof, while still retaining miR-438-3p biological activity (e.g., high levels of expression being associated with a malignant adrenocortical tumor).

MicroRNA-483-5p: A small non-coding RNA located on human chromosome 11. MicroRNA-483-5p is also known as miR-483-5p, miRNA483-5p and hsa-mir-483-5p. The expression of miR-483-5p has been linked to malignant adrenocortical tumors. Mir-483-5p expression is increased in malignant adrenocortical tumors as compared to benign adrenocortical tumors.

miR-483-5p sequences are publicly available, for example, GENBANK® Accession number NR_030158 (human miR-483-5p, nucleic acids 8-29) and miRBase Accession numbers MIMAT0004761 or MI0002467, each of which is incorporated by reference in its entirety as available on GENBANK® or miRBase, respectively, on Dec. 6, 2010. One skilled in the art will appreciate that miR-483-5p nucleic acid molecules can vary from those publicly available, such as polymorphisms resulting in one or more substitutions, deletions, insertions, or combinations thereof, while still retaining miR-438-5p biological activity (e.g., high levels of expression being associated with a malignant adrenocortical tumor).

Patient or Subject: As used herein, the term "patient" includes human and non-human animals, such as those having an adrenocortical tumor. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds, molecules or agents, such as those that alter the expression or activity of the molecules listed in Table 2 (such as decrease expression or activity of those increased in Table 2 and increase expression or activity of those decreased in Table 2).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Small interfering RNA (siRNA): A double-stranded nucleic acid molecule that modulates gene expression through the RNAi pathway (see, for example, Bass, *Nature* 411:428-9, 2001; Elbashir et al., *Nature* 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of a miR gene product.

Therapeutic or therapy: A generic term that includes both diagnosis and treatment. Treatment refers to a prescribed course of action (including administration of therapeutic agents) to alter the normal course of a disorder.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. In some examples, the therapeutic agent includes an isolated miR gene product that is down-regulated in patients with ACC or an inhibitor of an miR and/or mRNA that is up-regulated in patients with ACC.

Therapeutically effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

An amount of a composition that alone, or together with an additional therapeutic agent(s) (for example a chemotherapeutic agent), induces the desired response (e.g., treatment of a tumor, such as a malignant adrenocortical tumor). The preparations disclosed herein are administered in therapeutically effective amounts. In one example, a desired response is to decrease tumor size or metastasis in a subject to whom the therapy is administered. Tumor metastasis does not need to be completely eliminated for the composition to be effective. For example, a composition can decrease metastasis by a desired amount, for example by at least 20%, at least 50%, at least 60%, at least 70%, at least 80%, at least 90%, at least 95%, at least 98%, or even at least 100% (elimination of the tumor), as compared to metastasis in the absence of the composition.

In particular examples, it is an amount of a therapeutic agent effective to decrease a number of malignant adrenocortical carcinoma cells, such as in a subject to whom it is administered, for example a subject having one or more carcinomas. The cancer cells do not need to be completely eliminated for the composition to be effective. For example, a composition can decrease the number of cancer cells by a desired amount, for example by at least 20%, at least 50%, at least 60%, at least 70%, at least 80%, at least 90%, at least 95%, at least 98%, or even at least 100% (elimination of detectable cancer cells), as compared to the number of cancer cells in the absence of the composition.

In other examples, it is an amount of an agent capable of modulating one or more of the disclosed miRNA and/or mRNAs associated with a malignant adrenocortical tumor (such as associated with ACC) by least 20%, at least 50%, at least 60%, at least 70%, at least 80%, at least 90%, at least 95%, at least 98%, or even at least 100% (elimination of detectable tumor growth) by the therapeutic agent.

Tissue: A plurality of functionally related cells. A tissue can be a suspension, a semi-solid, or solid. Tissue includes cells collected from a subject, such as from the adrenal cortex.

Treating or ameliorating a disease: "Treating" refers to a therapeutic intervention that ameliorates a sign or symptom of a disease or pathological condition after it has begun to develop. "Ameliorating" refers to the reduction in the number or severity of signs or symptoms of a disease.

Tumor, neoplasia, malignancy or cancer: The result of abnormal and uncontrolled growth of cells. Neoplasia, malignancy, cancer and tumor are often used interchangeably and refer to abnormal growth of a tissue or cells that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Upregulated or activated: When used in reference to the expression of a nucleic acid molecule (such as a microRNA or mRNA), refers to any process which results in an increase in production of a gene product. In the context of the present disclosure, a gene product can be a primary transcript microRNA (pri-miRNA), precursor microRNA (pre-miRNA), a mature microRNA, mRNA, rRNA, tRNA, structural RNA or protein. Gene upregulation or activation includes any detectable increase in any of these molecules. In certain examples, production of a microRNA or mRNA increases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control. In some examples, a control is a relative amount of microRNA or mRNA expression in one or more subjects who do not have adrenocortical cancer or have a benign adrenocortical cancer.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Weiss criteria: A combination of the following nine criteria for distinguishing malignant adrenocortical tumors from benign adrenocortical tumors: nuclear grade III or IV; mitotic rate greater than 5/50 high-power fields; atypical mitoses; clear cells comprising 25% or less of the tumor; a diffuse architecture; microscopic necrosis; and invasion of venous, sinusoidal, and capsular structures. The presence of three or more of these features in a given tumor indicates malignant potential.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In addition, all GenBank accession numbers and miRBase accession numbers are herein incorporated by reference as they appear in the database on Dec. 6, 2010. In case of conflict, the present specification, including explanations of terms, will control. In addition, the materials, methods, and examples are illustrative only and not intended to be limiting.

II. Overview of Several Embodiments

Described herein is the identification of microRNAs and mRNAs that are differentially expressed in patients with malignant adrenocortical tumors, such as patients with ACC, compared with patients with benign adrenocortical tumors or healthy control subjects. Using microarray expression analysis, numerous microRNAs were identified that were up- or down-regulated at least 2-fold in patients with a malignant adrenocortical tumor relative to a control (e.g., a benign adrenocortical tumor or a healthy subject). Moreover, specific mRNAs were also identified to be up-regulated in malignant adrenocortical tumor samples. In some cases, miR-100, miR-125b, miR-195, miR-483-3p and miR-483-5p expression was altered by at least 2-fold. In some cases, IGF2 mRNA was increased by at least 2-fold in malignant adrenocortical tumor samples. Thus, by measuring expression of one or more of the differentially expressed microRNAs and/or mRNAs in a subject, one can diagnose a subject as having a malignant adrenocortical tumor, and more particularly ACC. The miRNAs and/or mRNAs identified as being differentially expressed in a malignant adrenocortical tumor as compared to a control may serve as therapeutic targets for treating the malignant adrenocortical tumor (including ACC).

A. Methods of Diagnosing a Malignant Adrenocortical Tumor

Provided herein is a method of diagnosing a subject as having a malignant adrenocortical tumor by measuring the level of at least one microRNA (miR) gene product or mRNA, such as IGF2 mRNA, in a biological sample of the subject. In some embodiments, the at least one miR gene product includes any miR gene product listed in any one of Table 2, FIG. 2 and FIG. 3. In particular embodiments, the at least one miR gene product is a miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p gene product. An alteration in the level of the at least one miR gene product in the biological sample of the subject relative to a control indicates the subject has a malignant adrenocortical tumor. As described herein, an increase in the level of miR-665, an increase in the level of miR-1246, an increase in the level of miR-483-5p, an increase in the level of miR-483-3p, an increase in the level of miR-642, an increase in the level of miR-1308, a decrease in the level of miR-1290, a decrease in the level of miR-600, a decrease in the level of let-7a, a decrease in the level of miR-195, a decrease in the level of miR-126, a decrease in the level of miR-125a-5p, a decrease in the level of miR-125b, a decrease in the level of miR-26a, a decrease in the level of miR-193b, a decrease in the level of let-7d, a decrease in the level of miR-29a, a decrease in the level of let-7f, a decrease in the level of miR-34a, a decrease in the level of let-7g, a decrease in the level of miR-26b, a decrease in the level of miR-214, a decrease in the level of miR-768-5p or a decrease in the level of miR-786-3p gene product, or a combination thereof, in a biological sample obtained from a subject with a adrenocortical tumor relative to a control (such as RNU48), indicates the subject has a malignant adrenocortical tumor. In particular embodiments, an increase in the amount of miR-483-5p, an increase in the amount of miR-483-3p, a decrease in the amount of miR-100, a decrease in the amount of miR-125b, a decrease in the amount of miR-195, an increase in IGF2 mRNA, or a combination thereof, in a biological sample obtained from a subject with a adrenocortical tumor relative to a control (such as RNU48), indicates the subject has a malignant adrenocortical tumor. In some embodiments, the increase or decrease in the level of the miR or mRNA is of a diagnostically significant amount.

In some embodiments of the methods, the diagnostically significant increase or decrease in expression of the miR gene product is at least 2-fold, such as at least 3-fold, at least 4-fold, at least 5-fold, at least 10-fold, including about 3-fold, about 4-fold, about 5-fold, about 6-fold, about 7-fold, about 8-fold, about 9-fold, about 10-fold, about 30-fold, and about 100-fold. In particular examples, miR-483-5p is increased by at least 2-fold, miR-483-3p is increased by at least 2-fold, miR-100 is decreased by at least 2-fold, miR-125b is decreased by at least 2-fold, miR-195 is decreased by at least 2-fold, IGF2 mRNA is increased by at least 2-fold, or a combination thereof, in the biological sample of the subject with a malignant adrenocortical tumor relative to the control (such as RNU48).

Figure 2:
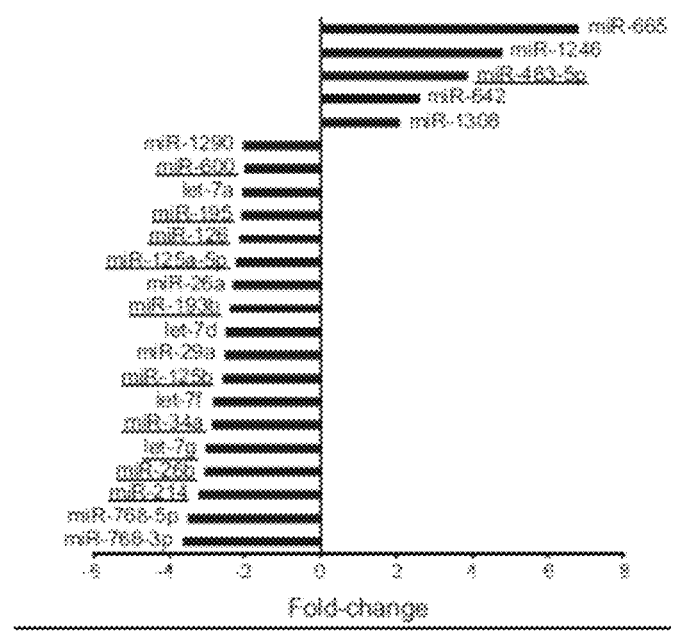
FIG. 2 shows the identification of differentially expressed miRNAs using microarray analysis. Unsupervised clustering was performed on the 50 most variable miRNAs. The most variable miRNAs were defined by the greatest absolute deviation from the mean across all samples. The Pearson correlation coefficient was used as the similarity metric in this analysis.

It is understood that the methods disclosed herein include measuring the level of any single miR gene product, or any combination or subcombination of the miR gene products listed in Table 2, FIG. 2 and FIG. 3. In particular examples, the combination of miR gene products includes a miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p gene product or any subcombination thereof. In other examples, the combination of miR gene products includes miR-100, miR-483-3p, miR-483-5p, miR-195 and miR-125b, or any subcombination thereof. In other examples, the combination of miR gene products includes miR-483-3p and miR-483-5p.

In some cases, the method includes measuring the level of a single miR gene product. In one example, the single miR gene product is miR-483-5p. In another example, the single miR gene product is miR-100. In another example, the single miR gene product is miR-195. In another example, the single miR gene product is miR-125b.

In some cases, the method includes measuring the level of one or more miR gene products described herein and one or more mRNAs known to be associated with ACC. In some embodiments, the method includes measuring the level of one or more miR gene products described herein and a single mRNA, such IGF2 mRNA. In further embodiments, the method includes measuring the level of a single miR gene product and a single mRNA. In one example, the single miR gene product is miR-483-5p and the single mRNA is IGF2. In another example, the single miR gene product is miR-483-3p and the single mRNA is IGF2. In another example, the single miR gene product is miR-100 and the single mRNA is IGF2. In another example, the single miR gene product is miR-195 and the single mRNA is IGF2. In another example, the single miR gene product is miR-125b and the single mRNA is IGF2.

Methods of detecting and measuring miR and mRNA expression are well known in the art and are described in detail below. In some examples, RT-PCR is used to measure the level of a miR or mRNA, such as when a single miR or mRNA is analyzed. In other cases, when multiple miR gene products and/or mRNAs are to be measured, it is desirable to use microarray analysis.

The miR gene product measured can be a primary miRNA (pri-miRNA) precursor miRNA (pre-miRNA), or a mature miRNA (including minor mature miRNA products denoted miR*).

In some embodiments of the methods, the biological sample is a tissue sample from the adrenal cortex. In some embodiments, the biological sample is blood, or a component thereof, such as plasma or serum.

In some embodiments, the method further includes providing an appropriate therapy for the subject diagnosed with a malignant adrenocortical tumor. In some examples, the therapy includes administering an agent that inhibits expression of a miR gene product, such as an agent that inhibits a miR gene product identified as up-regulated in a malignant adrenocortical tumor relative to a control. In other examples, the therapy includes administering an agent that includes administering an isolated miR gene product, such a miR gene product that has been identified as down-regulated in malignant adrenocortical tumors relative to a control. As a paragraph noting patients with an adrenocortical tumor, or suspected of having such, can be pre-selected for the treatment and screening methods herein.

B. Methods of Treating a Malignant Adrenocortical Tumor

Also provided herein is a method of treating a patient with a malignant adrenocortical tumor, including ACC, by administering to the patient a therapeutically effective amount of an agent that inhibits expression of a miR gene product and/or mRNA that is up-regulated in the patient with a malignant adrenocortical tumor relative to a control, or by administering to the patient a therapeutically effective amount of an isolated miR gene product that is down-regulated in the patient with a malignant adrenocortical tumor relative to a control.

In some embodiments, the miR gene product up-regulated in a malignant adrenocortical tumor, including ACC, is any miR gene product shown in Table 2 or FIG. 2 to be increased or up-regulated. In some embodiments, the miR gene product up-regulated in a malignant adrenocortical tumor, including ACC, is miR-665, miR-1246, miR-483-5p, miR-483-3p or miR-642. In particular examples, the up-regulated miR gene product is miR-483-3p or miR-483-5p. In one example, the up-regulated miR gene product is miR-483-5p. In some embodiments, the up-regulated mRNA in a malignant adrenocortical tumor, including ACC, is IGF2 mRNA. The agent can be any compound, such as a nucleic acid molecule, polypeptide, small molecule or other compound that is capable of inhibiting expression of one or more miR gene products or mRNAs up-regulated in an adrenocortical tumor. In some embodiments, the agent that inhibits expression of a miR gene product or mRNA is an antisense compound specific for the miR gene product. In some examples, the antisense compound is an antisense oligonucleotide, siRNA or ribozyme.

In some embodiments, the miR gene product down-regulated in a malignant adrenocortical tumor, including ACC, is any gene product shown in Table 2, FIG. 2 and FIG. 3 to be decreased or down-regulated. In some particular embodiments, the miR gene product down-regulated in a malignant adrenocortical tumor, including ACC, miR-1290, miR-600, let-7a, miR-195, a miR-126, miR-125a-5p, miR-125b, miR-26a, miR-193b, let-7d, miR-29a, let-7f, miR-34a, let-7g, miR-26b, miR-214, miR-768-5p or miR-786-3p gene product. In particular examples, the down-regulated miR gene product is a miR-100, miR-125b or miR-195 gene product. In some examples, administration of the isolated miR gene product comprises administering a vector encoding the miR gene product, such as a plasmid vector or a viral vector. In other embodiments, the isolated miR gene product can be delivered, for example, as naked miR or using a liposomal formulation (e.g., the miR can be encapsulated in a liposome), cationic lipids or a polypeptide carrier.

Further provided is the use of the expression level of at least one miR gene product and/or at least one mRNA in a biological sample of a subject for the diagnosis of the subject as having a malignant adrenocortical tumor and/or the treatment of the subject with a malignant adrenocortical tumor wherein the at least one miR gene product is a miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p gene product and the at least one mRNA is IGF2, and wherein: (i) an increase in the level of miR-665, an increase in the level of miR-1246, an increase in the level of miR-483-5p, an increase in the level of miR-483-3p, an increase in the level of miR-642, an increase in the level of miR-1308, a decrease in the level of miR-1290, a decrease in the level of miR-600, a decrease in the level of let-7a, a decrease in the level of miR-195, a decrease in the level of miR-126, a decrease in the level of miR-125a-5p, a decrease in the level of miR-125b, a decrease in the level of miR-26a, a decrease in the level of miR-193b, a decrease in the level of let-7d, a decrease in the level of miR-29a, a decrease in the level of let-7f, a decrease in the level of miR-34a, a decrease in the level of let-7g, a decrease in the level of miR-26b, a decrease in the level of miR-214, a decrease in the level of miR-768-5p, a decrease in the level of miR-786-3p gene product, an increase in IGF2 mRNA, or any combination thereof, in the biological sample of the subject relative to a control, indicates the subject has a malignant adrenocortical tumor, wherein the increase or decrease is of a diagnostically significant amount; and/or (ii) administering to the patient a therapeutically effective amount of an agent that inhibits expression of a mRNA or miR gene product that is up-regulated in the patient with a malignant adrenocortical tumor relative to a control, or by administering to the patient a therapeutically effective amount of an isolated miR gene product that is down-regulated in the patient with a malignant adrenocortical tumor relative to a control. In some embodiments, the use further includes providing an appropriate therapy or a second appropriate therapy for the subject diagnosed with a malignant adrenocortical tumor. In some particular embodiments, the method is used to diagnose ACC and treat a subject with ACC.

Also provided is the use of a therapeutically effective amount of an agent that inhibits expression of a miR gene product that is up-regulated in the patient with a malignant adrenocortical tumor, including ACC, relative to a control, or a therapeutically effective amount of an isolated miR gene product that is down-regulated in the patient with a malignant adrenocortical tumor, including ACC, relative to a control, in the preparation of a medicament for the treatment of a patient with a malignant adrenocortical tumor, such as for the treatment of ACC.

A therapeutically effective amount of an agent that inhibits expression of a miR gene product that is up-regulated in the patient with a malignant adrenocortical tumor, including ACC, relative to a control, or a therapeutically effective amount of an isolated miR gene product that is down-regulated in the patient with a malignant adrenocortical tumor, including ACC, relative to a control for use in a method for the treatment of a malignant adrenocortical tumor, including ACC, is further provided.

For the diagnosis and treatment methods disclosed herein, the control can be any suitable control, such as a reference value. For example, the reference value (or values if more than one mRNA or miR gene product is measured) can be an historical value based on average expression of the mRNA or miR gene product in a benign adrenocortical tumor or a healthy subject (a subject that has not been diagnosed with a malignant adrenocortical tumor, including ACC). In some examples, a control is an mRNA, small RNA or miRNA that is least variably expressed between malignant and benign adrenocortical tumors. In some examples, a small RNA, such as RNU48, RNU6, or RNU6b is used as the control. In some examples, miRs-1285, -34c-5p, or -542-3p are used as controls. In one particular example, RNU48 is used as the control used when determining differential expression of miRNAs. In some examples, a control is biological sample obtained from a benign adrenocortical tumor or a healthy subject.

C. In Vitro Process for Screening Therapeutic Agents for the Treatment of a Malignant Adrenocortical Tumor Also provided herein is an in vitro process for screening therapeutic agents for the treatment of a malignant adrenocortical tumor, including treatment of ACC, comprising: (i) contacting a cell culture with a candidate agent; and (ii) measuring the level of at least one miR gene product selected from miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p gene product and optionally measuring the level of at least IGF2 mRNA is IGF2, wherein a decrease in the level of miR-665, miR-1246, miR-483-5p, miR-483-3p, miR-642, miR-1308, IGF2 mRNA and/or an increase in the level of miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p relative to a control identifies a candidate agent as a therapeutic agent for the treatment of a malignant adrenocortical tumor, including for the treatment of ACC.

D. Methods for Screening Therapeutic Agents for the Treatment of a Malignant Adrenocortical Tumor Also provided is the use of the expression level of at least one miR gene product and/or mRNA for screening therapeutic agents for the treatment of a patient with a malignant adrenocortical tumor, including ACC, wherein the at least one miR gene product is miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p gene product, and the at least one mRNA is IGF2 mRNA, and wherein an agent that decreases the level of miR-665, miR-1246, miR-483-5p, miR-483-3p, miR-642, miR-1308, or IGF2 mRNA and/or an increases the level of miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p is a therapeutic agent for the treatment of a malignant adrenocortical tumor, including ACC. For example, if a miRNA or mRNA is up-regulated in a malignant adrenocortical tumor, including ACC, and an agent that decreases expression or activity by at least 20%, such as at least 30%, at least 40%, at least 50%, at least 60%, or at least 70%, including about a 20%, about a 25, about a 30%, about a 40%, about a 50%, about a 60%, about a 70%, about a 80%, or about a 90% decrease, indicates an effective treatment. Further, if a miRNA or mRNA is down-regulated in a malignant adrenocortical tumor, including ACC, and an agent that increases such expression or activity by at least 20%, such as at least 30%, at least 40%, at least 50%, at least 60%, or at least 70%, including about a 20%, about a 25, about a 30%, about a 40%, about a 50%, about a 60%, about a 70%, about a 80%, or about a 90% increase, indicates an effective treatment.

In some examples, an effective treatment is an at least 20%, such as at least 30%, at least 40%, at least 50%, at least 60%, or at least 70%, including about a 20%, about a 25, about a 30%, about a 40%, about a 50%, about a 60%, about a 70%, about a 80%, about a 90% decrease in expression of miR-483-3p, miR-483-5p, IGF2 mRNA or a combination thereof is measured. In some examples, an effective treatment is one in which an at least 20%, such as at least 30%, at least 40%, at least 50%, at least 60%, or at least 70%, including about a 20%, about a 25, about a 30%, about a 40%, about a 50%, about a 60%, about a 70%, about a 80%, about a 90% increase in expression of miR-100, miR-125b, miR-195 or a combination thereof is measured.

E. Arrays

Also provided are arrays, such as arrays for diagnosing and determining the effectiveness of a malignant adrenocortical tumor. In some examples, an array includes at least two oligonucleotides that specifically hybridize with an mRNA and/or miR gene product associated with a malignant adrenocortical tumor, including ACC, is disclosed. In some embodiments, an array includes at least two oligonucleotides that specifically hybridize with an mRNA, such as IGF2 mRNA, and/or a miR gene product selected from the miR gene products listed in any one of Table 2, FIG. 2 and FIG. 3 is also provided. In some embodiments, the array includes at least two oligonucleotides that specifically hybridize with a miR gene product selected from the group consisting essentially of, or consisting of miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p. Further provided is the use of such arrays for selecting an appropriate therapy for a subject with a malignant adrenocortical tumor, including ACC. The arrays can also be used to monitor the course of a selected therapy to determine whether the therapy is effective for the treatment of the malignant adrenocortical tumor, including ACC, as evidence by an increase or decrease in the level of one or more miRs associated with a malignant adrenocortical tumor (including ACC), such as a decrease in miR-483-5p, miR-483-3p or a combination thereof or an increase in miR-100, miR-125b, miR-195 or a combination thereof.

In some examples such arrays further include control probes, such as those that permit detection of at least 1 housekeeping gene (such as (3-action, GADPH, RNU48, RNU44, U18 or U47), for example 1 to 5 or 1-10 housekeeping genes.

F. Kits

Also provided are kits including at least two oligonucleotide probes specific for a miR gene product selected from the miR gene products listed in any one of Table 2, FIG. 2 and FIG. 3 and/or IGF2 mRNA. In some embodiments, the kits include at least two oligonucleotide probes specific for IGF2 mRNA and a miR gene product selected from the group consisting of miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p. In some embodiments, the kits include at least two oligonucleotide probes specific at least two miR gene products selected from the group consisting of miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p, such as probes specific for at least miR-483-5p and miR100. In some examples, the kit includes controls (such as positive and negative controls).

i. Adrenal Tumors

Adrenal tumors can be benign or malignant adrenal tumors. Malignant adrenal tumors include neuroblastoma, adrenocortical carcinoma (ACC), and a minority of adrenal pheochromocytomas. Most adrenal pheochromocytomas and all adrenocortical adenomas are benign tumors, which do not metastasize or invade nearby tissues, but which may still cause significant health problems by giving rise to hormonal imbalances. Disclosed herein are particular miRNAs and mRNAs which can be used to diagnosis a subject with a malignant adrenal tumor, such as ACC as these molecules are differentially expressed in malignant adrenal cortex tumors as compared to benign adrenal cortex tumors.

Adrenocortical carcinoma is an aggressive cancer originating in the cortex (steroid hormone-producing tissue) of the adrenal gland. Adrenocortical carcinoma is a rare tumor with an incidence of 1-2 per million population annually. Adenocortical carcinoma is often associated with hormonal syndromes which can occur in patients with steroid hormone-producing ("functional") tumors, including Cushing's syndrome, Conn syndrome, virilization and feminization. Due to their location deep in the retroperitneum, most adrenocortical carcinomas are not diagnosed until they have grown quite large. They frequently invade large vessels, such as the renal vein and inferior vena cava, as well as metastasizing via the lymphatics and through the blood to the lungs and other organs. The most effective treatment currently is surgery, although this is not feasible for many patients, and the overall prognosis of the disease is poor. Chemotherapy, radiation therapy and hormonal therapy may also be employed in the treatment of this disease.

In contrast, adrenocortical adenomas are benign tumors of the adrenal cortex which are extremely common (present in 1-10% of persons at autopsy). The clinical significance of these neoplasms is twofold. First, they have been detected as incidental findings with increasing frequency in recent years, due to the increasing use of CT scans and magnetic resonance imaging in a variety of medical settings. This can result in expensive additional testing and invasive procedures to rule out the slight possibility of an early adrenocortical carcinoma. Second, a minority (about 15%) of adrenocortical adenomas are "functional", meaning that they produce glucocorticoids, mineralcorticoids, and/or sex steroids, resulting in endocrine disorders such as Cushing's syndrome, Conn's syndrome (hyperaldosteronism), virilization of females, or feminization of males. Functional adrenocortical adenomas are surgically curable.

Most of the adrenocortical adenomas are less than 2 cm in greatest dimension and less than 50 g in weight. However, size and weight of the adrenal cortical tumors are no longer considered to be a reliable sign of benignity or malignancy. Grossly, adrenocortical adenomas are encapsulated, well-circumscribed, solitary tumors with solid, homogeneous yellow-cut surface. Necrosis and hemorrhage are rare findings.

Pheochromocytoma is a neoplasm composed of cells similar to the chromaffin cells of the mature adrenal medulla. Pheochromocytomas occur in patients of all ages, and may be sporadic, or associated with a hereditary cancer syndrome, such as multiple endocrine neoplasia (MEN) types IIA and IID, neurofibromatosis type I, or von Rippel-Lindau syndrome. Only 10% of adrenal pheochromocytomas are malignant, while the rest are benign tumors. The most clinically important feature of pheochromocytomas is their tendency to produce large amounts of the catecholamine hormones epinephrine (adrenaline) and norepinephrine. This may lead to potentially life-threatening high blood pressure, or cardiac arrythmias, and numerous symptoms such as headache, palpitations, anxiety attacks, sweating, weight loss and tremor. Diagnosis is often confirmed through urinary measurement of catecholamine metabolites. Typically, pheochromocytomas are initially treated with anti-adrenergic drugs to protect against catecholamine overload, with surgery employed to remove the tumor once the patient is medically stable.

ii. MicroRNA Nomenclature and Nucleotide Sequences

MicroRNAs (also known as miRNAs and miRs) are short RNA sequences expressed from longer transcripts found in the genomes of animals, plants and viruses and at least one single-celled eukaryote (Molnar et al., *Nature* 447:1126-1129, 2007; Zhao et al., *Genes Dev.* 21:1190-1203, 2007). MicroRNAs regulate the expression of target genes by binding to complementary sites in the target gene transcripts to cause translational repression or transcript degradation (Pillai et al., *Trends Cell Biol.* 17:118-126, 2007). These small RNA molecules have been implicated in a number of biological processes related to development, cell proliferation, apoptosis, metabolism, morphogenesis and disease (particularly cancer) (Kloosterman and Plasterk, *Dev. Cell* 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs).

A nomenclature scheme has been well established for microRNAs (Griffiths-Jones et al., *Nucleic Acids Res.* 34:D140-D144, 2006; Ambros et al., *RNA* 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "100," resulting in a complete name of "hsa-miR-100." As used herein, miRNAs not denoted by a specific prefix such as "hsa" can include multiple species, such as human and mouse. Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-125a and miR-125b). In some cases, mature miRNAs from both the 5' and 3' arms of the hairpin precursor are identified, which are designated "3p" or "5p" (such as miR-483-3p and miR-483-5p). Viral microRNA names relate to the locus from which the microRNA is derived (for example, ebv-miR-BART1 is from the Epstein-Barr virus BART locus).

MicroRNA gene product sequences are well described throughout the scientific and patent literature and are available online through miRBase (www.mirbase.org), provided by the University of Manchester (previously provided by the Sanger Institute). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR*.

iii. Detecting miRNA and mRNA Expression Associated with Malignant Adrenocortical Tumors As described below, expression of one or more miRNAs or mRNAs associated with a malignant adrenocortical tumor can be detected using any one of a number of methods well known in the art. In some embodiments of the methods provided herein, microRNA and/or mRNA expression profiles are used to diagnose malignant adrenocortical tumors and to predict the prognosis and develop potential therapies for patients with malignant adrenocortical tumors, such as to treat ACC.

Thus, the disclosed methods can include evaluating miRNA, such as those illustrated in FIGS. 2-3 (including, but not limited to miR-100, miR-125b, miR-195, miR-483-3p or miR-483-5p). In some embodiments, the methods provided herein further include evaluating expression of mRNA, such as IGF2 mRNA. In some examples, the miRNA and/or mRNA are quantified.

The sequences of precursor microRNAs and mature miRNAs are publicly available, such as through the miRBase database, available online by the University of Manchester, and formerly maintained by the Sanger Institute (see Griffiths-Jones et al., *Nucleic Acids Res.* 36:D154-D158, 2008; Griffiths-Jones et al., *Nucleic Acids Res.* 34:D140-D144, 2006; and Griffiths-Jones, *Nucleic Acids Res.* 32:D109-D111, 2004). The sequences of particular mRNAs, such as IGF2 mRNA are also publicly available, such as through GENBANK®.

Detection and quantification of microRNA and/or mRNA expression can be achieved by any one of a number of methods well known in the art including those described herein (such as Example 1). U.S. Patent Application Publication Nos. 2006/0211000 and 2007/0299030 describe methods of miRNA detection and quantification. Further, general methods for mRNA extraction are well known in the art and are disclosed in standard textbooks of molecular biology, including Ausubel et al., Current Protocols of Molecular Biology, John Wiley and Sons (1997). Using the known sequences for a microRNA or mRNA of interest, specific probes and primers can be designed for use in the detection methods described herein as appropriate.

In some cases, the microRNA and/or mRNA detection method requires isolation of nucleic acid from a sample, such as a cell, biological fluid sample or tissue sample (for example, a tissue biopsy from the adrenal cortex). Nucleic acids, including RNA and specifically miRNA or mRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain mRNA, miRNAs and siRNAs.

Microarray analysis of microRNAs or mRNAs can be accomplished according to any method known in the art (see, for example, PCT Publication No. WO 2008/054828; Ye et al., *Nat. Med.* 9(4):416-423, 2003; Calin et al., *N. Engl. J. Med.* 353(17):1793-1801, 2005). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding microRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing miRNA extracted from a cell, biological fluid or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described herein.

Any one of a number of methods for detecting expression of a gene of interest (including microRNAs or mRNAs) known in the art can be used to detect expression of a microRNA or mRNA. A number of these methods, including qRT-PCR, array, microarray, in situ hybridization, in situ PCR, SAGE are described in further detail below. miRNA detection can also be accomplished by deep sequencing, according to methods known in the art (Creighton et al., *Brief Bioinform.* 10(5):490-2009 Ma497, 2009).

a. RT-PCR

Methods for quantitating RNA, including microRNA or mRNA, are well known in the art. In some embodiments, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. TaqMan® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

The steps of a representative protocol for quantitating gene expression using fixed, paraffin-embedded tissues as the RNA source, including RNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 μm thick sections of paraffin-embedded tissue samples. The RNA is then extracted, and protein and DNA are removed. Alternatively, RNA is located directly from a tissue, cell or fluid sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as a microRNA or mRNA. Primers that can be used to amplify a particular microRNA or mRNA are commercially available (in some instance) or can be designed and synthesized according to well known methods using publically available sequences of the microRNA or mRNA.

b. Serial Analysis of Gene Expression (SAGE)

SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

c. In Situ Hybridization (ISH)

ISH is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of microRNAs or mRNA.

Sample cells or tissues are treated to increase their permeability to allow a probe, such as microRNA-specific probe or a mRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a adrenal cortex tissue sample. Since the sequences of the microRNAs or mRNAs of interest are known, probes can be designed accordingly such that the probes specifically bind the gene of interest.

d. In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

e. Arrays for Profiling MicroRNA and/or mRNA Expression

In particular embodiments provided herein, arrays can be used to evaluate microRNA and/or mRNA expression, for example to diagnose or prognose adrenocortical tumors, including ACC. When describing an array that comprises probes or primers specific for a particular set of microRNAs or mRNAs, such an array includes probes or primers specific for the recited microRNAs (such as those provided in FIGS. 2A-3, including but not limited to miR-100, miR-125b, miR-195, miR-483-3p and miR-483-5p) and/or mRNAs (such as IGF2 mRNA), and can further include control probes (for example to confirm the incubation conditions are sufficient). Exemplary control probes include GAPDH, RNU48, actin, and YWHAZ. In one example, an array is a multi-well plate (e.g., 98 or 364 well plate).

In one example, the array includes, consists essentially of, or consists of probes or primers that can recognize the miRNAs listed in Table 2, FIG. 2 or FIG. 3 and RNU48 for a control probe. In some examples, the array includes, consists essentially of, or consists of probes or primers that can recognize the miRNAs listed in Table 2, FIG. 2 or FIG. 3, RNU48 (a control probe) and probes or primers that can recognize IGF2 mRNA. In certain examples, the array includes at least probes or primers that can recognize miRNA-483-5p (for example, probes and primers that can recognize miRNA-483-5p and at least one of miRNA-483-3p, miRNA-100, miRNA-125b, or miRNA-195) and RNU48. In certain examples, the array includes at least probes or primers that can recognize miRNA-483-5p and probes and primers that can recognize IGF2 mRNA (for example, probes and primers specific for miRNA-483-5p and probes and primers specific for IGF2 mRNA and at least one of the additional miRNAs listed in Table 2, FIG. 2 or FIG. 3, such as miRNA-483-3p, miRNA-100, miRNA-125b, or miRNA-195) and a control probe such as RNU48 or GAPDH. The oligonucleotide probes or primers can further include one or more detectable labels, to permit detection of hybridization signals between the probe and target sequence (such as one of the microRNAs disclosed herein).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al., Anal. Biochem. 217:306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the wells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

f. Output of miR or mRNA Gene Expression Analysis Results

Gene expression can be evaluated using any technique described above, or any other method known in the art. As described herein, gene expression can be measured, for example, using labeled probes that can be detected using standard equipment. For example, gene expression measurements using microarray or RT-PCR (which typically use labeled probes specific for a gene product) can be quantitated using a microarray scanner or other suitable scanner for detecting the label. In some embodiments, the device used to measure gene expression is a microarray scanner. Microarray scanners are well known and are commercially available, such as the Model G250 GB Microarray Scanner from Agilent Technologies.

The results of gene expression analysis can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the data is recorded in a patient's electronic medical record.

iv. Modulating MicroRNA Expression for Treatment of a Malignant Adrenocortical Tumor It is disclosed herein that many microRNAs are differentially expressed in patients with a malignant adrenocortical tumor, including patients with ACC. As such, an increase in the level of one or more microRNAs down-regulated in patients with a malignant adrenocortical tumor, or a decrease in the level of one or more microRNAs up-regulated in patients with a malignant adrenocortical tumor may be beneficial for inhibiting the development or progression of a malignant adrenocortical tumor and/or for alleviating one or more signs or symptoms of a malignant adrenocortical tumor (for example, decreased tumor growth).

Without wishing to be bound by theory, it is believed that alterations in the level of one or more miR gene products in cells can result in the deregulation of one or more intended targets for these miRs, which can lead to the development or progression of a malignant adrenocortical tumor, including the development and progression of ACC. Therefore, altering the level of the miR gene product (e.g., by decreasing the level of a miR that is up-regulated in a malignant adrenocortical tumor or by increasing the level of a miR that is down-regulated in a malignant adrenocortical tumor) may successfully treat or ameliorate one or more signs or symptoms of malignant adrenocortical tumor, such as treat or ameliorate one or more signs or symptoms associated with ACC.

a. Use of Agents that Inhibit Up-Regulated MicroRNAs

Provided herein is a method of treating a patient with a malignant adrenocortical tumor by administering to the patient a therapeutically effective amount of an agent that inhibits expression of a miR gene product that is up-regulated in patients with malignant adrenocortical tumors compared with a control (such as a benign adrenocortical tumor or a healthy control subject).

As used herein, "inhibiting expression of miR gene product" means that the production of the precursor and/or active, mature form of the miR gene product after treatment is less than the amount produced prior to treatment. One skilled in the art can readily determine whether miR expression has been inhibited in a subject, using the techniques known in the art and described herein. Inhibition can occur at the level of gene expression (i.e., by inhibiting transcription of a miR gene encoding the miR gene product) or at the level of processing (e.g., by inhibiting processing of a miR precursor into a mature miR).

As used herein, a therapeutically effective amount of a compound that inhibits miR expression is an amount sufficient to result in a biological effect (such as alleviating one or more signs or symptoms of a malignant adrenocortical tumor, including one or more signs or symptoms associated with ACC). For example, an agent can decrease or increase the expression level of a target miR by a desired amount, for example by at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value. In some examples, the therapeutically effective amount is that which results in at least a 2-fold alteration in one or more miRNAs listed in FIGS. 2A-3 (such as a two-fold decrease in a miRNA-483-5p and/or miRNA-483-3p and/or a 2-fold increase in miRNA-100, miRNA-125b, miRNA-195).

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression of miR gene product.

In some embodiments, a single agent that inhibits expression of a miR gene product is administered to the subject in need of treatment. In other embodiments, two or more agents (such as 2, 3, 4, 5, 6, 7, 8, 9 or 10 or more) that inhibit expression of a miR gene product are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an agent that inhibits miR expression can be administered to a subject in combination with one or more additional treatments for a malignant adrenocortical tumor, including ACC. Exemplary ACC treatments include, but are not limited to, administration of one or more chemotherapeutic agents, such as mitotane (an inhibitor of steroid synthesis which is toxic to cells of the adrenal cortex) as well as standard cytotoxic drugs. For example, an exemplary regimen includes an agent that inhibits miR expression administered to a subject in combination with cisplatin, doxorubicin, etoposide, and mitotane. In some examples, the endocrine cell toxin streptozotocin is also included. In further examples, hormonal therapy with steroid synthesis inhibitors such as aminoglutethimide is used in a palliative manner to reduce the symptoms of hormonal syndromes associated with the ACC.

An agent that inhibits expression of a miR gene product can be any type of compound, such as, but not limited to, a nucleic acid molecule, polypeptide, antibody or small molecule, that is capable of inhibiting expression of one or more miR gene products. In some embodiments, the agent is an antisense compound.

Any type of antisense compound that specifically targets a miR gene product is contemplated for use to inhibit expression of the target miR gene product. In some examples, the agent is an antisense compound selected from an antisense oligonucleotide, a siRNA, or a ribozyme. Methods of designing, preparing and using antisense compounds are within the abilities of one of skill in the art. Furthermore, sequences for the disclosed miR gene products are publicly available. Antisense compounds specifically targeting a miR that is differentially expressed in a malignant adrenocortical tumor, such as ACC, (or other target nucleic acid) can be prepared by designing compounds that are complementary to the target nucleotide sequence, such as a pri-microRNA, pre-microRNA or mature microRNA sequence. Antisense compounds need not be 100% complementary to the target nucleic acid molecule to specifically hybridize with the target nucleic acid molecule. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

Generally, the principle behind antisense technology is that an antisense compound hybridizes to a target nucleic acid and effects the modulation of gene expression activity or function. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a miR gene product.

Each of the above-described antisense compounds provides sequence-specific target gene regulation. This sequence-specificity makes antisense compounds effective tools for the selective modulation of a target nucleic acid of interest, such as a miR gene product.

In some embodiments, the antisense compounds are antisense oligonucleotides. The miR gene product-specific antisense oligonucleotides can be any suitable length to allow for hybridization and modulation of gene expression. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target miR gene product. As used herein, an siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a miR gene product, and which is able to specifically cleave the miR gene product. The substrate binding region need not be 100% complementary to the target miR gene product. For example, the substrate binding region can be, for example, at least about 50%, at least about 75%, at least about 85%, or at least about 95% complementary to a contiguous nucleic acid sequence in a miR gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector, as described in further detail below in regard to expression of isolated miR gene products. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, *Science* 261:1004, 1993; Werner and Uhlenbeck, *Nucl. Acids Res.* 23:2092-2096, 1995; Hammann et al., *Antisense and Nucleic Acid Drug Dev.* 9:25-31).

In some examples, the antisense compounds specific for a miR gene product contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (*Science* 254, 1497-1500, 1991).

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta.*, 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

b. Use of Nucleic Acid Molecules Encoding Down-Regulated MicroRNAs

Also provided is a method of treating a patient with a malignant adrenocortical tumor (such as a patient with ACC) by administering to the patient a therapeutically effective amount of an isolated microRNA gene product that is down-regulated in a patient with a malignant adrenocortical tumor, including ACC, relative to a control (such as a benign adrenocortical tumor or a healthy subject). For example, a subject with a malignant adrenocortical tumor, including ACC, is treated by administering a therapeutically effective amount of an isolated miR-100, miR-125b or miR-195 gene product. As described herein, the miR gene product can be a pri-miRNA, a pre-miRNA or a mature miRNA.

The disclosed methods comprise administering an effective amount of at least one isolated miR gene product, or an isolated variant or biologically-active fragment thereof. The isolated miR gene product that is administered to the subject can be identical to an endogenous wild-type miR gene product (such as a pri-miRNA, pre-miRNA or mature miRNA) that is down-regulated in the patient with a malignant adrenocortical tumor, or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule) and inhibition of a cellular process associated with a malignant adrenocortical tumor (e.g., increased levels of glucocorticoids, mineralcorticoids, and/or sex steroids, virilization of females, or feminization of males). These variants include species variants and variants that are the consequence of one or more mutations (e.g., a substitution, a deletion, an insertion) in a miR gene. In certain embodiments, the variant is at least about 70%, at least about 75%, at least about 80%, at least about 85%, at least about 90%, at least about 95%, at least about 98%, or at about 99% identical to a corresponding wild-type miR gene product.

As used herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with a malignant adrenocortical tumor, including ACC. In certain embodiments, the biologically-active fragment is at least about 9, at least about 11, at least about 13, at least about 15, at least about 17 or at least about 19 nucleotides in length.

A therapeutically effective amount of an isolated gene product can be, for example, the amount necessary to alleviate one or more signs or symptoms of a malignant adrenocortical tumor, including one or more signs or symptoms of ACC, and/or the amount required to delay progression of the disease. One of skill in the art can determine the amount of an isolated miR gene product required for therapeutic efficacy.

In some embodiments, a single isolated miR gene product is administered to the subject in need of treatment. In other embodiments, two or more miR gene products (such as 2, 3, 4, 5, 6, 7, 8, 9 or 10 or more) are administered to the subject. When two or more miR gene products are administered to the subject, the miR gene products can be administered simultaneously (or within quick succession, such as within minutes of each other), or they can be administered at different times. For example, two or more miR gene products can be administered one hour, twelve hours, one day, two days, five days, one week, two weeks or one month apart.

In some embodiments, an isolated miR gene product can be administered to a subject in combination with one or more additional treatments for a malignant adrenocortical tumor, such as ACC. Exemplary ACC treatments include, but are not limited to, administration of one or more chemotherapeutic agents and hormonal regulatory agents (as described herein, including Section VIII below).

As used herein, an "isolated" miR gene product is one that is synthesized, or is purified away from other biological components of the cell or tissue in which the miR naturally occurs. For example, a synthetic miR gene product, or a miR gene product partially or completely separated from the other biological components of its natural state is considered to be "isolated." Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, for example, Proligo (Hamburg, Germany), Dharmacon Research (Lafayette, Colo.), Pierce Chemical (Rockford, Ill.), Glen Research (Sterling, VS), ChemGenes (Ashland, Mass.) and Cruachem (Glasgow, United Kingdom).

In some embodiments, the method includes administering a vector encoding a miR gene product. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miR gene products are expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the invention can also comprise inducible or regulatable promoters for expression of the miR gene products.

When two or more miR gene products are to be expressed, the miR gene products can each be expressed from separate recombinant plasmids, or they can be expressed from the same recombinant plasmid. In one embodiment, the miR gene products are expressed as RNA precursor molecules from a single plasmid, and the precursor molecules are processed into the functional miR gene product within the target cell. Selection of plasmids suitable for expressing the miR gene products, methods for inserting nucleic acid sequences into the plasmid to express the gene products, and methods of delivering the recombinant plasmid to the cells of interest are within the skill in the art (see, for example, Zeng et al., *Mol. Cell.* 9:1327-1333, 2002; Tuschl, *Nat. Biotechnol.,* 20:446-448, 2002; Brummelkarnp et al., *Science* 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002). In one embodiment, a plasmid expressing the miR gene product comprises a sequence encoding a miR precursor RNA operably linked to the CMV intermediate-early promoter.

The miR gene products can also be expressed from recombinant viral vectors. When administering two or more miR gene products, it is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in target cells or tissues of a patient with a malignant adrenocortical tumor, such as a patient with ACC.

The recombinant viral vectors of use with the disclosed methods include sequences encoding the miR gene products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the invention can also comprise inducible or regulatable promoters for expression of the miR gene products.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Zern and Kresinam, *Hepatology* 25(2), 484-491, 1997). Representative adenoviral vectors which can be used for the methods provided herein are described by Stratford-Perricaudet et al. (*J. Clin. Invest.* 90: 626-630, 1992); Graham and Prevec (*In Methods in Molecular Biology: Gene Transfer and Expression Protocols* 7: 109-128, 1991); and Barr et al. (*Gene Therapy*, 2:151-155, 1995).

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,6741 6,613,892; 6,692,955; 6,344,445; 6,319,703; and 6,261,552; and U.S. Patent Application Publication No. 2003-0083289).

As used herein, a "therapeutically effective amount" of an isolated miR gene product is an amount sufficient to result in a biological effect (such as alleviating one or more signs or symptoms of a malignant adrenocortical tumor, including alleviating one or more signs or symptoms of ACC). One skilled in the art can readily determine a therapeutically effective amount of a miR gene product to be administered to a given subject, by taking into account factors, such as the size and weight of the subject; the extent of disease progression; the age, health and sex of the subject; the route of administration; and whether the administration is regional or systemic.

For example, an effective amount of an isolated miR gene product can be based on the approximate body weight of a subject to be treated. Such effective amounts can be administered by any suitable route, such as, for example, parenterally or enterally. In some examples, a therapeutically effective amount of the isolated miR gene product that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

c. Administration of Therapeutic Agents

Therapeutic agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some embodiments, the therapeutic agent is a nucleic acid molecule, such as a miR gene product, a vector encoding a miR gene product, an antisense compound or a vector encoding an antisense compound. A nucleic acid-based therapeutic agent can be administered to a subject by any suitable route. In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In the context of the present disclosure, a miR gene product or an antisense compound can be administered to the subject either as naked RNA or DNA in combination with a delivery reagent, or can be encoded by a recombinant plasmid or viral vector. Recombinant plasmids and viral vectors including sequences that express the miR gene products or antisense compounds, and techniques for delivering such plasmids and vectors to target cells, are well known in the art.

In some embodiments, liposomes are used to deliver a miR gene product or antisense compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a miR gene product or antisense compound to a subject. Cationic lipids and polymers that can be used to deliver therapeutic RNA molecules have been described (see, for example, Zhang et al., *J Control Release.* 123(1):1-10, 2007; Vorhies et al., *Methods Mol. Biol.* 480:11-29, 2009; and U.S. Patent Application Publication No. 2009/0306194). Polypeptide carriers can also be used to administer a miR gene product to a subject (see, for example, Rahbek et al., *J. Gene Med.* 10:81-93, 2008).

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

v. Combination Treatment Methods

The disclosed therapies for inhibiting or treating malignant adrenocortical tumors can be used alone or can be accompanied by administration of other anti-cancer agents or therapeutic treatments (such as surgical resection of a tumor or radiation therapy). Any suitable anti-cancer agent can be administered to a patient as part of a treatment regimen that includes inhibiting or treating a malignant adrenocortical tumor. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and antibodies that specifically target cancer cells.

Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Examples of antimetabolites include folic acid analogs (such as methotrexate), pyrimidine analogs (such as 5-FU or cytarabine), and purine analogs, such as mercaptopurine or thioguanine.

Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase).

Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of many of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

In some examples, the chemotherapy regimen includes mitotane (an inhibitor of steroid synthesis which is toxic to cells of the adrenal cortex) as well as standard cytotoxic drugs. For example, an exemplary regimen consists of cisplatin, doxorubicin, etoposide, and mitotane. In some examples, the endocrine cell toxin streptozotocin is included with the chemotherapeutic. In further examples, hormonal therapy with steroid synthesis inhibitors such as aminoglutethimide is used in a palliative manner to reduce the symptoms of hormonal syndromes associated with the ACC.

When used in combination with the administration of one of the disclosed therapeutic agents targeting one or more of miRNAs and/or mRNAs associated with a malignant adrenocortical tumor (e.g., associated with ACC), the additional treatment methods described above can be administered or performed prior to, at the same time, or following the disclosed anti-tumor therapy as appropriate for the particular patient, the additional symptoms associated with the ACC (e.g., hormonal symptoms, conditions and related diseases) and the specific combination of therapies.

vi. Tissue Samples

The methods provided herein include detecting expression of one or more miRNA or mRNA in adrenocortical tissue samples. In some embodiments, the tissue samples are obtained from subjects diagnosed with an adrenocortical tumor, such as a malignant adrenocortical tumor or a benign adrenocortical tumor. In some cases, the tissue samples are obtained from healthy subjects or cadaveric donors. A "sample" refers to part of a tissue that is either the entire tissue, or a diseased or healthy portion of the tissue. As described herein, malignant tumor tissue samples are compared to a control. In some embodiments, the control is a benign adrenocortical tumor obtained from a different subject. In some embodiments, the control is non-cancerous tissue sample obtained from the same subject, such as a benign tumor adjacent to the tumor. In other embodiments, the control is non-cancerous tissue sample obtained from the same subject, such as non-cancerous tissue surrounding the malignant tumor. In other embodiments, the control is an adrenocortical tissue sample obtained from a healthy patient or a non-cancerous tissue sample from a cadaver. In other embodiments, the reference sample is a standard or reference value based on an average of historical values.

Tissue samples can be obtained from a subject using any method known in the art. For example, tissue samples can be obtained from ACC patients who have undergone tumor resection as a form of treatment. From these patients, both tumor tissue and surrounding non-cancerous tissue can be obtained. In some embodiments, the non-cancerous tissue sample used as a control is obtained from a cadaver.

In some embodiments, tissue samples are obtained by biopsy. Biopsy samples can be fresh, frozen or fixed, such as formalin-fixed and paraffin embedded. Samples can be removed from a patient surgically, by extraction (for example by hypodermic or other types of needles), by microdissection, by laser capture, or by any other means known in the art.

The following examples are provided to illustrate certain particular features and/or embodiments. These examples should not be construed to limit the disclosure to the particular features or embodiments described.

EXAMPLES

Example 1

Materials and Methods

This is example describes the material and methods used to perform the studies in Examples 2-7.

Tissue Samples.

Adrenocortical tissue samples were procured at the time of surgery, snap frozen in liquid nitrogen, and stored at −80° C. Patient and tumor characteristics used for miRNA microarray profiling are summarized in Table 1. Tumors were classified as adrenocortical carcinoma when gross local invasion and/or metastasis (lymph or distant) was present at the time of diagnosis or occurred during follow-up. Localized tumors with no evidence of recurrence at follow-up (mean 2.1 years) were classified as benign. An independent set of benign (n=35), locoregional ACC recurrences (n=2), and ACC metastases (n=29) tumor samples were used for validation. Normal adrenal glands were procured from healthy organ donors under an IRB approved protocol (n=21). Laser capture microdissection was used to isolate tissue from the cortex.

TABLE 1

Clinical Features of Microarray Samples

|  | Adrenocortical Carcinoma | Benign Adrenocortical Tumor |
|---|---|---|
| Number of Patients | 10 | 26 |
| Age (Ave. ± STD) | 45.1 ± 21.3 | 50.1 ± 13.2 |
| Sex (Female/Male) | 7/3 | 19/7 |
| Syndrome: |  |  |
| Cushing's | 7 | 8 |
| Subclinical Cushing's | 0 | 2 |
| Conn's | 0 | 4 |
| Nonfunctioning | 3 | 12 |

RNA Extraction and Quality Control.

Total RNA was extracted from frozen tissue. RNA integrity and quality was confirmed using an Agilent 2100 Bioanalyzer. All RNA samples used for miRNA profiling had a RNA integrity number >5.

miRNA Microarray Expression Profiling and Data Analysis.

A total of 36 microarrays were run comparing either benign adrenocortical tumors (n=26) or ACCs (n=10) to a common reference pool of 21 normal adrenal cortices. For each array, 300 ng of total RNA (either tumor or reference) was labeled with Cy5 or Cy3 using the miRCURY LNA microRNA Array Labeling Kit (Exiqon, Denmark). Cy5 and Cy3 samples were combined such that all tumor samples were compared to normal pooled. In 12 samples, the reference normal pooled sample was labeled with Cy5 (dye swap). Fluorescently labeled RNA was hybridized to Exiqon miR-CURY LNA miRNA arrays (v. 11.0) using SureHyb DNA microarray hybridization chambers and gasket slides (Agilent, Santa Clara, Calif.) for 18 hours at 56° C. Arrays were scanned on an Axon GenePix 4000B scanner (Molecular Devices, Sunnyvale, Calif.), and GenePix results files (GPR) containing fluorescence intensities were generated using GenePix Pro 6.0 software.

GPR files were loaded into R/Bioconductor using the marray package. Flagged spots were removed from subsequent analysis and the remaining probes were used for normalization and subsequent analyses. The $\log_2$ ratio of the intensity of Cy5 to Cy3 signals were calculated for each miRNA on every array (with no background subtraction) and normalized by print tip loess normalization. Since individual miRNAs were represented by four probes on the array, the median of normalized $\log_2$ ratio of the replicate probes (for those with more than one unflagged probe) was used as the value for the miRNA. The summarized $\log_2$ ratios for each study were then used in moderated t-statistics and p-value calculation using the limma package in R/Bioconductor with adjustment for false discovery rate using the Benjamini-Hochberg method.

Real-Time Quantitative RT-PCR Analysis.

MiRNAs that were found to be differentially expressed in the microarray experiments were validated using TaqMan quantitative real-time RT-PCR (Applied Biosystems, Foster City, Calif.). Single-stranded cDNA was synthesized from 5 ng of total RNA using specific miRNA primers (TaqMan MicroRNA Assay, PN 4427975, Applied Biosystems) and the TaqMan MicroRNA Reverse Transcription Kit (PN 4366596, Applied Biosystems). Two microliters of cDNA was used as a template in a 10 µL PCR reaction. PCR products were amplified using specific primers (TaqMan MicroRNA Assay) and the TaqMan Universal PCR Master Mix (PN 4324018, Applied Biosystems) and detected using 7900HT Fast Real-Time PCR System (Applied Biosystems). PCR reactions for each sample were run in triplicate. Control reactions included cDNA synthesized without reverse transcriptase enzyme (RNA only) and no cDNA template. The following TaqMan MicroRNA Assays used in this study were obtained from Applied Biosystems: let-7g (002282), miR-26b (000407), miR-483-5p (002338), miR-214 (002306), miR-195 (000494), miR-193b (002367), miR-126 (002228), miR-125b (000449), miR-125a-5p (002198), miR-30b (000602), miR-34a (000426), and miR-100 (000437). RNU48 (001006), RNU6b (001093), U6 (001973), miR-34c (000428), miR-542-3p (001284), and miR-1285 (002822) were tested as possible endogenous controls for data normalization by measuring their expression in all of the samples. The prediction algorithm NormFinder was used to analyze expression stability of the possible controls.

For measuring IGF2 expression in patient samples, single-stranded cDNA was synthesized from 100 ng of total RNA. TaqMan Real-time quantitative PCR was used to measure IGF2 mRNA expression level relative to glyceraldehyde-3-phosphate dehydrogenase (GAPDH) mRNA expression. The TaqMan probes for the IGF2 (Hs01005970_ml) and GAPDH (Hs99999905_ml) were obtained from Applied Biosystems. All the PCR was performed in a final volume of 10 µL, with 2 µL of cDNA template, using TaqMan Universal Master Mix (PN 4440043, Applied Biosystems) on a 7900HT Fast Real-Time PCR System (Applied Biosystems).

MiRNA expression level was expressed as the difference between cycle threshold ($C_t$) for the miRNA of interest and that of RNU48 ($\Delta C_t$). IGF2 mRNA expression level was expressed as the difference between cycle threshold ($C_t$) for IGF2 and that of GAPDH ($\Delta C_t$). Since the sample sizes were small, the Mann-Whitney U test was used to assess statistical significance. A p-value of less than 0.05 was considered statistically significant.

This work identified microRNAs that are differentially expressed in malignant adrenocortical tumors as compared to benign tumors. Significantly, miR-483-5p appears to be a defining characteristic of adrenocortical malignancies and expression of miR-483-5p can be used to accurately distinguish between benign and malignant adrenocortical tumors.

Example 2

Identification of Differentially Expressed miRNAs

This example describes the identification of differentially expressed miRNAs in ACCs and benign adrenocorcial tumors.

The global miRNA profiles were obtained for the samples listed in Table 1 which included 10 primary adrenocortical carcinomas (ACCs) and 26 benign adrenocortical tumors. A total of 36 microarrays were performed comparing the total RNA from each individual tumor sample to a common reference pool of RNA from 21 normal adrenal cortices. All 36 arrays were of adequate quality for analysis.

The difference between tumors and normal adrenocortical tissue was determined. Differentially expressed miRNAs were defined as those that had an adjusted p-value of less than 0.01 as described in the Materials and Methods (Example 1). There were a similar number of differentially expressed human miRNAs in both benign and malignant tumors as compared to normal (82 and 71, respectively) (FIG. 1). Only 17 miRNAs were differentially expressed in both comparisons suggesting that benign and malignant tumors have relatively distinct patterns of miRNA dysregulation. For the majority of the 17 common miRNAs, the fold change in expression was more dramatic in ACC. For example, in comparison to normal tissue, miR-100 was downregulated 1.5-fold in benign tumors whereas in malignant tumors it was 2.6-fold lower.

Example 3

Unsupervised Cluster Analysis of the Most Differentially Expressed miRNAs

This example describes unsupervised cluster analysis of the most differentially expressed miRNAs detected in Example 2.

The microarray design compared each tumor sample to a common reference (pooled normal), thereby allowing for direct assessment of the miRNA expression differences between benign and malignant adrenocortical tumors. The fifty most variable miRNAs are provided in Table 2 below. Each of the miBase Accession numbers provided are incorporated by reference as available on Dec. 6, 2010 in the miBase Database.

TABLE 2

50 most variable miRNAs (used for unsupervised clustering)

| miRNA | Expression in malignant as compared to benign | Exemplary miRBase Accession Nos. |
|---|---|---|
| hsa-miRPlus-E1047 | down | |
| hsa-miR-125b/mmu-miR-125b-5p/rno-miR-125b-5p | down | MI0000446; MI0000470 |
| hsa-miR-143/mmu-miR-143/rno-miR-143 | down | MI0000459; MI0000257 |

TABLE 2-continued 50 most variable miRNAs (used for unsupervised clustering)

| miRNA | Expression in malignant as compared to benign | Exemplary miRBase Accession Nos. |
|---|---|---|
| hsa-miR-29a/mmu-miR-29a/rno-miR-29a | down | MI0000087; MI0000576; MI0000863 |
| hsa-miR-23b | down | MI0000439 |
| hsa-miRPlus-E1141 | down | |
| hsa-miR-193b | down | MI0003137 |
| hsa-miRPlus-E1202 | down | |
| hsa-miR-195/mmu-miR-195/rno-miR-195 | down | MI0000489; MI0000237; MI0000939 |
| hsa-miR-100/mmu-miR-100/rno-miR-100 | down | MI0000102; MI0000692 |
| hsa-miR-214/mmu-miR-214/rno-miR-214 | down | MI0000290; MI0000698; MI0000954 |
| mmu-miR-23b/rno-miR-23b | down | MI0000141; MI0000853; MI0000439 |
| hsa-miR-22/mmu-miR-22/rno-miR-22 | down | MI0000078; MI0000570; MI0000851 |
| hsa-miR-24/mmu-miR-24/rno-miR-24 | down | MI0000080; MI000008; MI0000231; MI0000854; MI0008545 |
| hsa-miR-768-3p | down | MI0005117 |
| hsa-miR-768-5p | down | MI0005117 |
| hsa-miRPlus-E1172 | down | |
| hsa-miR-30a/mmu-miR-30a/rno-miR-30a | down | MI0000088; MI0000144; MI0000870 |
| hsa-miR-16/mmu-miR-16/rno-miR-16 | down | MI0000070; MI0000115; MI0000844 |
| hsa-miR-23a/mmu-miR-23a/rno-miR-23a | down | MI0000079; MI0000571; MI0000852 |
| hsa-miR-923 | down | MI0005715 |
| hsa-miR-130a/mmu-miR-130a/rno-miR-130a | down | MI0000448; MI0000156; MI0000903 |
| hsa-miR-34a/mmu-miR-34a/rno-miR-34a | down | MI0000268; MI0000564; MI0000877 |
| hsa-miR-1827 | down | MI0008195 |
| mmu-miR-21*/rno-miR-21* | down | MI0000569; MI0000850; MI0000077 |
| hsa-miR-99b/mmu-miR-99b/rno-miR-99b | down | MI0000746; MI0000147; MI0000884 |
| hsa-miR-637 | down | MI0003652 |
| mmu-miR-669f | down | MI0006287 |
| mmu-miR-466c-5p | down | MI0005505; MI0014057 |
| mmu-miR-665 | down | MI0014057 |
| hsa-miR-1259 | down | MI0006393 |
| hsa-miR-642 | down | MI0003657; MI0016685 |
| hsa-miRPlus-E1212 | down | |
| mmu-miR-669e | down | MI0006300 |
| hsa-miR-1290 | down | MI0006352 |
| hsa-miR-320c | down | MI0003778; MI0008191 |
| hsa-miRPlus-E1060 | up | |
| hsa-miRPlus-F1216 | up | |
| hsa-miRPlus-E1290 | up | |
| hsa-miRPlus-E1136 | up | |
| mmu-miR-467e* | up | MI0006128 |
| hsa-miR-320b | up | MI0003776; MI0003839 |
| hsa-let-7i/mmu-let-7i/rno-let-7i | up | MI0000434; MI0000138; MI0000835 |
| hsa-miRPlus-A1083 | up | |
| mmu-miR-467g | up | MI0006301 |
| hsa-miRPlus-F1187 | up | |
| hsa-miR-138/mmu-miR-138/rno-miR-138 | up | MI0000455; MI0000476; MI0000722; MI0000911; MI0000912 |
| hsa-miR-1246 | up | MI0006381 |
| hsa-miR-665 | up | MI0005563 |
| hsa-miRPlus-F1086 | up | |

Unsupervised clustering was performed on the top 50 most variable miRNAs. The resulting heatmap showed some structure, with the malignant samples clustering separately from the majority of the benign samples. However, miRNA expression profiles for a few of the benign samples were more similar to malignant. It is possible that for this subset of tumor samples that these tumors have more potential for malignant transformation.

Example 4

Validation of Differentially Expressed miRNAs

This example describes the validation of differentially expressed miRNAs described in Examples 2 and 3.

Using a stringent significance criteria of a 2-fold or greater difference in expression level and an adjusted p-value of less than 0.01, 23 miRNAs were found to be differentially expressed. Of these 23, 5 miRNAs had higher expression and 18 miRNAs had lower expression in ACC (FIG. 2). Thirteen of these top differentially expressed miRNAs were chosen for further study (FIGS. 1 and 2B, underlined). The 13 miRNAs were validated in the same samples used for the microarrays (10/10 malignant and 24/26 benign tumors; two benign samples had insufficient RNA and were excluded from validation) by real-time quantitative RT-PCR. The unnormalized PCR data for 12 of the miRNAs tested showed good correlation with the microarray data (p<0.0001). Data was not obtained for miR-600 because it was not amplified by PCR.

Two of the malignant tumor samples had evidence of necrosis and consistently had lower miRNA expression (higher raw $C_t$) across all of the tested miRNAs. Initially these types of tumors were included in the microarray studies since they were representative of the tumor tissue heterogeneity encountered in ACCs. In fact, in both benign and malignant samples a variable amount of fibrosis and tumor stroma were present in up to 20% of the tissue section. Given this tumor heterogeneity a good strategy for controlling the biological variations between samples was developed. "Invariant" small RNAs are often used as endogenous controls for miRNA quantitative RT-PCR data normalization. A panel of six possible normalizers; three small RNAs (RNU48, RNU6, and RNU6b) and three miRNAs that according to the microarray data were least variably expressed across all samples (miRs-1285, -34c-5p, and -542-3p) were tested. RNU48 was selected as the best control since it had the lowest standard deviation across all of the samples (raw C) and was the most stably expressed overall and across the sample subgroups (NormFinder).

The mean expression data normalized to RNU48 (AC) for benign tumors (n=24) and ACC (n=10) for the 12 validation miRNAs is shown in FIG. 3. For the most part, the overall trend observed by microarray analysis was recapitulated (higher expression of miR-483-5p (lower $\Delta C_t$) and lower expression of most of the other miRs (higher $\Delta C_t$)) in ACC as compared to benign tumors. Four of the miRNAs, miRs-483-5p, -195, -125b, and -100, had a statistically significant difference between the tumor types (Mann Whitney U test, p<0.05).

Example 5

Identification of a Diagnostic miRNA for ACC

This example describes the identification of a diagnostic miRNA (miR-483-5p) for ACC.

Figure 4A:
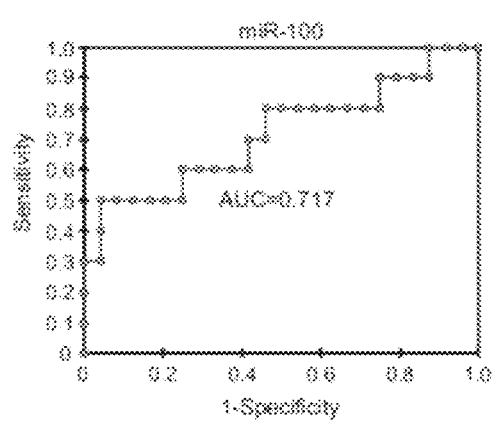
FIGS. 4A-4D are receiver operating characteristic curves (ROCs) plotted based on the real-time PCR expression profiling of miRs-100 (FIG. 4A), -125b (FIG. 4B), -195 (FIG. 4C), and -483-5p (FIG. 4D) (normalized to RNU48) for 34 samples (10 primary ACCs and 24 benign adrenocortical tumors). The area under the curve (AUC) was listed on the graph. With an AUC of 0.95, miR-483-5p had the greatest diagnostic accuracy (a perfect diagnostic marker without any false-negative or false-positives would have an AUC of 1).
Figure 4B:
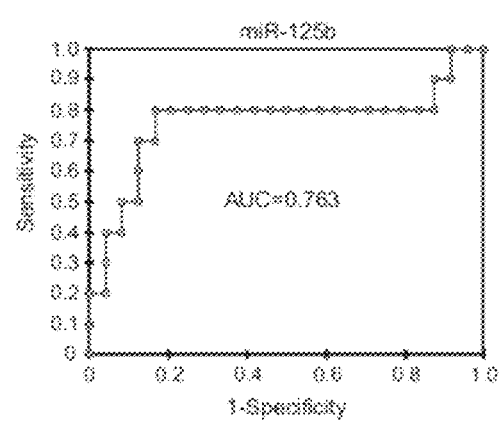
Figure 4C:
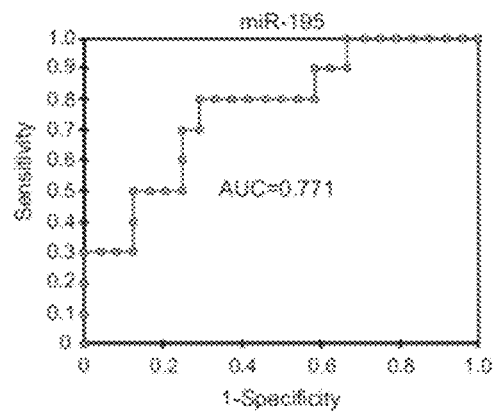
Figure 4D:
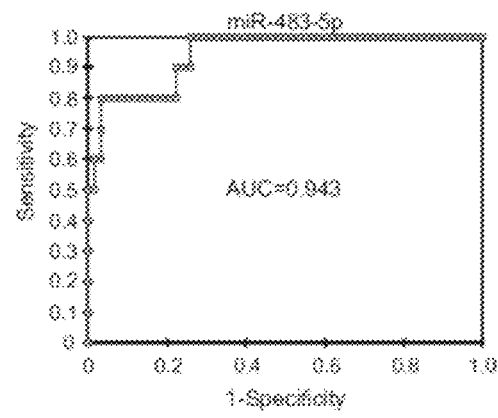

To determine the diagnostic accuracy of miRs-483-5p, -195, -125b, and -100, the area under the receiver operator characteristic curve (AUC) was calculated (FIGS. 4A-4D). MiR-483-5p had the highest AUC (0.95) indicating that the expression of this miRNA could accurately distinguish between benign tumors and ACCs (FIG. 4D). Combining miR-483-5p with the other miRNAs did not improve accuracy. Furthermore, classification based miR-483-5p expression alone in these same tumor samples (10 primary malignant and 23 benign tumors) resulted in 8 of 10 malignant samples being classified as malignant (80% sensitivity) and 24 of 24 truly benign samples being classified as benign (100% specificity). This results in a positive predictive value of 100% and a negative predictive value of 92%. These studies support the use of miR-483-5p as a diagnostic marker of ACC.

Example 6

Figure 5:
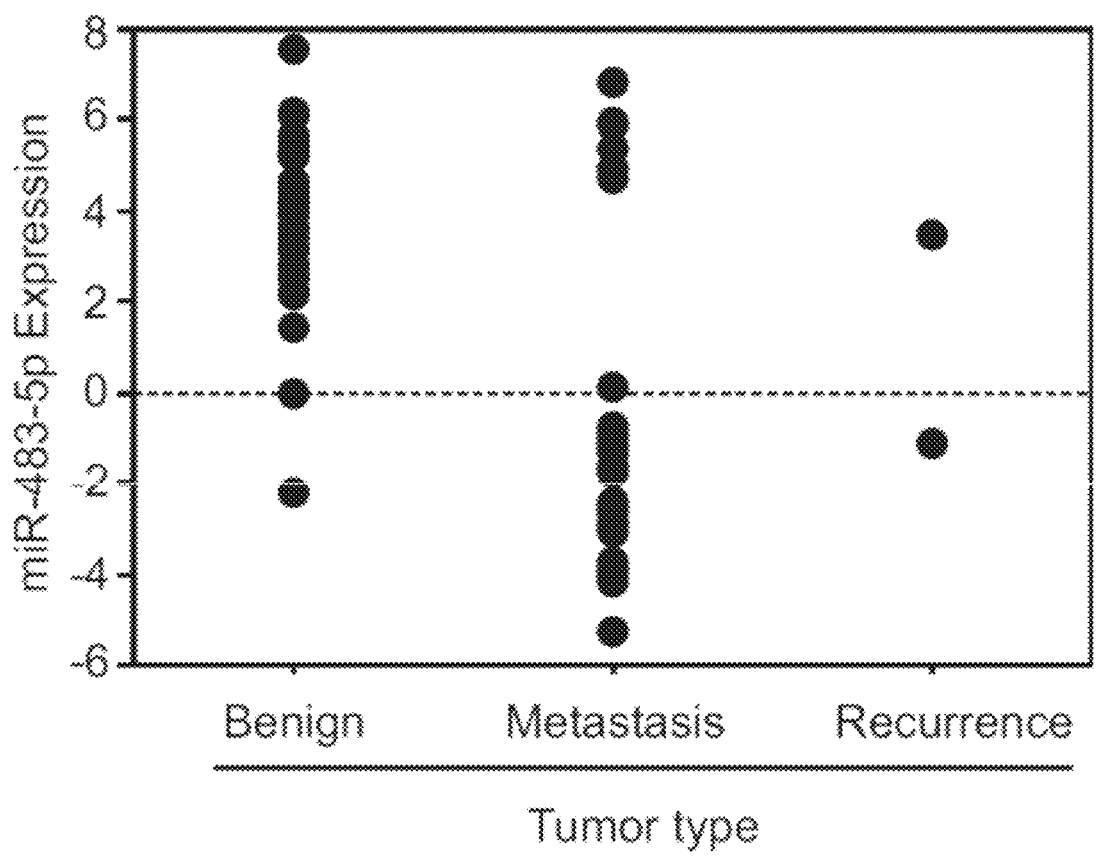
FIG. 5 is a plot showing high miR-483-5p expression associated with adrenocortical malignancy. Real-time quantitative RT-PCR was used to assay the expression of miR-483-5p in tumor samples, either benign (n=35) or malignant (ACC recurrence, n=2; ACC metastasis, n=29). Each individual point on the plot denotes a patient sample. The y-axis represents the expression of miR-483-5p which was expressed as the $\Delta C_t$ ($C_t$ miR-483-5p–$C_t$ RNU48). A lower $\Delta C_t$ (compare benign to malignant) indicated higher miRNA expression. There was a statistically significant difference between the benign and malignant groups (p<0.0001, Mann Whitney U test).

Increased miR-483-5p Expression is a Marker of Malignant Phenotype in Adrenocortical Tumors This example indicates increased miR-483-5p expression is a marker of malignant phenotype in adrenocortical tumors The disclosed data suggests that overexpression of miR-483-5p occurs frequently and consistently in primary ACCs. It was speculated that high expression of miR-483-5p may be a persistent and general characteristic of adrenocortical malignancy. To address whether high expression of miR-483-5p was a persistent and general characteristic of adrenocortical malignancy, the expression of miR-483-5p in an independent cohort of benign tumors (n=35), locoregional ACC recurrences (n=2), and ACC metastases (n=29) was measured by real-time quantitative RT-PCR. The majority of malignancies had higher expression of miR-483-5p (lower $\Delta C_t$) relative to the benign group and that this difference was statistically significant (p<0.0001, Mann Whitney U test) (FIG. 5). A small subset (7 out of 31) of the malignant samples had miR-483-5p expression that more closely resembled that of benign tumors. These samples came from various sites of metastases in four different ACC patients (these were the only samples from these patients included in this analysis). These patients' tumors responded well to chemotherapy and they had the best overall response among the group tested.

Based on miR-483-5p expression, the malignant samples formed two mutually exclusive groups; the majority highly expressed miR-483-5p (low $\Delta C_t$) and, as mentioned above, a small subset had lower expression of this miRNA (high $\Delta C_t$) (FIG. 5). The miR-483 locus maps to the epigenetically regulated IGF2 gene. Therefore, the dichotomous expression pattern observed may be reflective of the transcriptional status of the imprinted locus being either 'on' or 'off'. If this is the case, it also suggests that these tumors are rather homogenous, at least in terms of gene expression from this particular region.

Example 7

Increased miR-483 is Correlated with high IGF2 Expression in Adrenocortical Tumors This example shows increased miR-483 is correlated with high IGF2 expression in adrenocortical tumors.

Figure 6A:
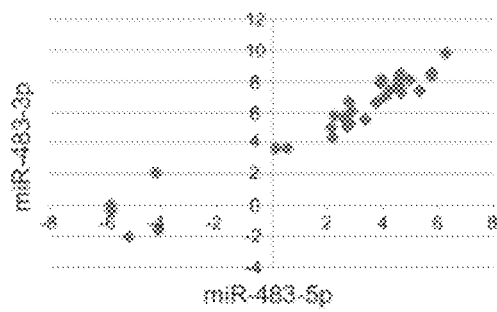
FIGS. 6A and 6B are graphs illustrating the expression of miR-483-3p, miR-483-5p, and IGF2 mRNA are highly correlated. Real-time quantitative RT-PCR was used to assay the expression of miR-483-3p in tumor samples, either benign (n=24) or malignant (primary, n=10).

MiR-483 is expressed from intron two of the IGF2 gene. Both the 5' and 3' arm of this precursor can express a mature miRNA (either miR-483-5p or miR-483-3p, respectively). Although our miRNA microarray did not identify miR-483-3p as differentially expressed between malignant and benign tumors, the expression of this miRNA was analyzed directly by real-time quantitative RT-PCR. Surprisingly, in a manner identical to miR-483-5p, miR-483-3p is highly expressed in malignant samples. In fact the expression of these two miRNAs are highly correlated (FIG. 6A, r=0.965).

IGF2 expression was measured in the same patient samples by real-time quantitative RT-PCR. Comparison of IGF2 mRNA and miR-483 expression showed a significant positive correlation (FIG. 6B, r=0.799) suggesting that they are coexpressed from this locus and could be used as indicators of ACC. The disclosed studies found that using miR-483-5p expression has a high negative predictive value of 92% suggesting that the majority of patients with negative test results would be correctly diagnosed.

Figure 6B:
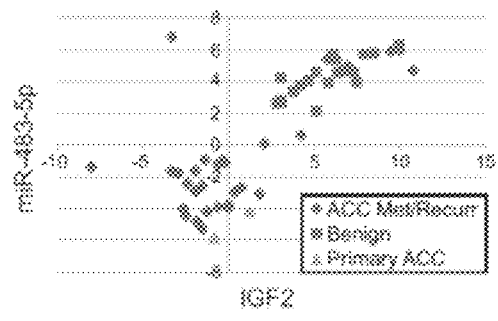

High expression of miR-483-5p is a common occurrence in primary and metastatic ACCs. The miR-483 gene locus has been mapped to intron two of IGF2. It was hypothesized that the high expression of miR-483-5p observed in ACC is an indirect consequence of IGF2 overexpression. In support of this, miR-483-5p appeared to be expressed concordantly with IGF2 mRNA (FIGS. 6A and 6B). Based on this, it is proposed that miR-483 expression could serve as a useful indicator of IGF2 expression. Clinical trials for ACC patients are evaluating therapies targeting the IGF signaling pathway because of promising preclinical studies that showed a significant antineoplastic effect from inhibiting IGF signaling. Assessing the miR-483 expression level from tumor samples or possibly even in serum may serve to quickly identify those patients that would most benefit from this type of therapy.

Example 8

Method to Treat ACC

This example describes a particular method that can be used to treat ACC in humans by administration of one or more agents that alter one or more of the disclosed miRNAs that are differentially expressed in ACC. Although particular methods, dosages, and modes of administrations are provided, one skilled in the art will appreciate that variations can be made without substantially affecting the treatment.

Based upon the teaching disclosed herein, ACC can be treated by administering a therapeutically effective amount of an agent that modulates the biological activity (including expression) of miR-483-3p or miR-483-5p and IGF2-mRNA, thereby reducing or eliminating the activity of the miR-483-3p or miR-483-5p and IGF2-mRNA which in reduces one or more signs or symptoms associated with the ACC.

Briefly, the method can include screening subjects to determine if they have a ACC. Subjects having ACC are selected. In one example, subjects having increased levels of miR-483-3p or miR-483-5p and IGF2-mRNA are selected. In one example, a clinical trial would include half of the subjects following the established protocol for treatment of ACC (such as a normal chemotherapy/radiotherapy/surgery regimen). The other half would follow the established protocol for treatment of the ACC (such as a normal chemotherapy/radiotherapy/surgery regimen) in combination with administration of the therapeutic compositions described above. In some examples, the tumor is surgically excised (in whole or part) prior to treatment with the therapeutic compositions. In another example, a clinical trial would include half of the subjects following the established protocol for treatment of ACC (such as a normal chemotherapy/radiotherapy/surgery regimen). The other half would follow the administration of the therapeutic compositions described above. In some examples, the tumor is surgically excised (in whole or part) prior to treatment with the therapeutic compositions.

Screening Subjects

In some examples, the subject is first screened to determine if they have ACC. In particular examples, the subject is screened to determine if the adrenocortical tumor is malignant, indicating ACC, or benign. Examples of methods that can be used to screening for ACC include a combination of ultrasound, tissue biopsy, and serum blood levels. If blood or a fraction thereof (such as serum) is used, 1-100 μl of blood is collected. Serum can either be used directly or fractionated using filter cut-offs to remove high molecular weight proteins. If desired, the serum can be frozen and thawed before use. If a tissue biopsy sample is used, 1-100 μg of tissue is obtained, for example using a fine needle aspirate. The biological sample (e.g., tissue biopsy or serum) is analyzed to determine expression of miR-483-3p or miR-483-5p and IGF2-mRNA, wherein the presence of such overexpression of miR-483-3p or miR-483-5p and IGF2-mRNA indicates that the tumor is malignant and further that it can be treated with the disclosed therapies.

In a specific example, a tissue biopsy is procured from the adrenal cortex. RNA is isolated and purified from these cells using routine methods, such as using the methods described in Example 1. Alterations in expression levels of miR-483-3p, miR-483-5p and IGF2 mRNA are determined by performing real-time PCR or microarray analysis (see, Example 1 for detailed procedure). Detection of an at least 2-fold increase in miR-483-3p, miR-483-5p and IGF2 mRNA relative to control values (e.g., expression levels in a benign adrenocortical tumor or a reference value known to be indicative of miR-483-3p, miR-483-5p and IGF2 mRNA expression levels in a benign adrenocortical tumor) is indicative that the subject has ACC and is a candidate for receiving the therapeutic compositions disclosed herein. However, such pre-screening is not required prior to administration of the therapeutic compositions disclosed herein (such as those that include an agent that alters expression of one or more miRNAs listed in any one of FIGS. 2A-3 and/or IGF2 mRNA).

Pre-Treatment of Subjects

In particular examples, the subject is treated prior to administration of a therapeutic composition that includes one or more agents to one or more of the disclosed miRNAs and/or mRNAs differentially expressed in a malignant adrenocortical tumor. However, such pre-treatment is not always required, and can be determined by a skilled clinician. For example, the tumor can be surgically excised (in total or in part) prior to administration of the therapy. In addition, the subject can be treated with an established protocol for treatment of the particular tumor present (such as a normal chemotherapy/radiotherapy regimen).

Administration of Therapeutic Compositions

Following subject selection, a therapeutic effective dose of the composition is administered to the subject, wherein the composition includes one or more siRNAs capable of inhibiting miR-483-3p, miR-483-5p and IGF2 mRNA. The siRNAs are complexed with polyethylenimines to form polyethylenimine/siRNA complexes. These complexes can then be delivered in vivo by intraperitoneal or subcutaneous injection at 20 to 2000 nM final siRNA concentration and internalized by tumor cells within a few hours leading to the intracellular release of siRNA molecules, which display full bioactivity.

Administration of the therapeutic compositions can be continued after chemotherapy and radiation therapy is stopped and can be taken long term (for example over a period of months or years).

Assessment

Following the administration of one or more therapies, subjects having a malignant tumor (for example ACC) can be monitored for tumor treatment, such as regression or reduction in metastatic lesions, tumor growth or vascularization. In particular examples, subjects are analyzed one or more times, starting 7 days following treatment. Subjects can be monitored using any method known in the art. For example, diagnostic imaging can be used (such as x-rays, CT scans, MRIs, ultrasound, fiber optic examination, and laparoscopic examination), as well as analysis of biological samples from the subject (for example analysis of blood, tissue biopsy, or other biological samples), such as analysis of the type of cells present, or analysis for a particular tumor marker. In one example, if the subject has advanced ACC, assessment can be made using ultrasound, MRI, or CAT scans, or analysis of the type of cells contained in a tissue biopsy. It is also contemplated that subjects can be monitored for the response of their tumor(s) to therapy during therapeutic treatment by at least the aforementioned methods.

Additional Treatments

In particular examples, if subjects are stable or have a minor, mixed or partial response to treatment, they can be re-treated after re-evaluation with the same schedule and preparation of agents that they previously received for the desired amount of time, such as up to a year of total therapy. A partial response is a reduction in size or growth of some tumors, but an increase in others.

Example 9

Diagnosis of a Malignant Adrenocortical Tumor

This example describes particular methods that can be used to diagnose or prognose a malignant adrenocortical tumor in a subject, such as ACC in a human. However, one skilled in the art will appreciate that similar methods can be used. In some examples, such diagnosis is performed before treating the subject (for example as described in Example 8).

A tissue biopsy sample is procured from the adrenal cortex of a subject suspected of having a malignant adrenocortical tumor. RNA is isolated and purified from these cells using routine methods, such as using the methods described in Example 1. Alteration in miR-483-3p, miR-483-5p and IGF2 mRNA are determined by performing real-time PCR (see, Example 1 for detailed procedure). Detection of an at least 2-fold increase in miR-483-3p, miR-483-5p and IGF2 mRNA relative to control values (e.g., expression levels in a benign adrenocortical tumor or a reference value known to be indicative of miR-483-3p, miR-483-5p and IGF2 mRNA expression levels in a benign adrenocortical tumor) is indicative that the subject has a malignant adrenocortical tumor.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of distinguishing malignant adrenocortical tumor from a benign adrenocortical tumor, comprising:
   providing an adrenocortical tumor sample
   measuring expression of at least one microRNA (miR) gene product, RNU4-8 and IGF2 mRNA in the adrenocortical tumor sample, wherein the at least one miR gene product comprises at least miR-483-5p; and
   identifying a malignant adrenocortical tumor, with a positive predictive value of 100% and a negative predictive value of 92% by detecting increased expression in at least one miR-483-5p relative to RNU48 expression and increased expression in IGF2 mRNA compared to a control in the tumor sample.

2. The method of claim 1, wherein the at least one miR gene product comprises miR-100, miR-665, miR-1246, miR-483-5p, miR-483-3p, miR-642, miR-1308, miR-1290, miR-600, let-7a, miR-195, miR-126, miR-125a-5p, miR-125b, miR-26a, miR-193b, let-7d, miR-29a, let-7f, miR-34a, let-7g, miR-26b, miR-214, miR-768-5p or miR-786-3p.

3. The method of claim 1, wherein one of the at least one miR gene product comprises miR-483-5p.

4. The method of claim 1, wherein the at least one miR gene product comprises miR-100, miR-125b, miR-195, miR-483-3p, miR-483-5p or a combination thereof.

5. The method of claim 1, wherein altered increased expression of at least one of the miR gene products comprises increased expression in at least one of miR-665, miR-1246, miR-483-5p, miR-483-3p, miR-642, miR-1308 or a combination thereof and increased expression in IGF2 mRNA.

6. The method of claim 5, wherein the increased expression comprises an at least 2-fold increase in expression in the sample obtained from the subject as compared to the control.

7. The method of claim 1, wherein increased expression of at least one of the miR gene products comprises increased expression in miR-483-3p, miR-483-5p, or a combination thereof.

8. The method of claim 1, wherein increased expression is measured by real time quantitative polymerase chain reaction or microarray analysis.

9. The method of claim 1, wherein the method is used for diagnosing or prognosing a subject with adrenocortical carcinoma.

10. A method of a distinguishing a malignant adrenocortical tumor from a benign adrenocortical tumor, comprising:
    measuring expression of at least miR-483-5p and IGF2 mRNA in a sample obtained from the subject with an adrenocortical tumor by contacting the sample with an miR-483-5p specific probe and an IGF2 probe; and
    identifying an increase in the expression of the at least miR-483-5p and IGF2 mRNA in the sample obtained from the subject as compared to a control indicates a malignant adrenocortical tumor, with a positive predictive value of 100% and a negative predictive value of 92%.

* * * * *